US010799401B2

(12) United States Patent
Matsumura

(10) Patent No.: US 10,799,401 B2
(45) Date of Patent: Oct. 13, 2020

(54) ABSORBENT ARTICLE AND METHOD FOR PRODUCING SAME

(71) Applicant: Daio Paper Corporation, Ehime (JP)

(72) Inventor: Takashi Matsumura, Tochigi (JP)

(73) Assignee: Daio Paper Corporation, Ehime (JP)

( * ) Notice: Subject to any disclaimer, the term of this patent is extended or adjusted under 35 U.S.C. 154(b) by 205 days.

(21) Appl. No.: 15/562,156

(22) PCT Filed: Mar. 25, 2016

(86) PCT No.: PCT/JP2016/059624

§ 371 (c)(1),
(2) Date: Sep. 27, 2017

(87) PCT Pub. No.: WO2016/158750

PCT Pub. Date: Oct. 6, 2016

(65) Prior Publication Data

US 2018/0078429 A1 Mar. 22, 2018

(30) Foreign Application Priority Data

Mar. 30, 2015 (JP) ................................ 2015-070293

(51) Int. Cl.
*A61F 13/49* (2006.01)
*A61F 13/496* (2006.01)
(Continued)

(52) U.S. Cl.
CPC ........ *A61F 13/49017* (2013.01); *A61F 13/15* (2013.01); *A61F 13/15601* (2013.01);
(Continued)

(58) Field of Classification Search
CPC combination set(s) only.
See application file for complete search history.

(56) References Cited

U.S. PATENT DOCUMENTS 5,470,639 A * 11/1995 Gessner .................... D01F 6/46 156/161
5,567,501 A * 10/1996 Srinivasan ............ D04H 1/558 428/137
(Continued)

FOREIGN PATENT DOCUMENTS

CN 101573092 3/2013
JP 2004298399 10/2004
(Continued)

OTHER PUBLICATIONS

International Search Report, PCT/JP2016/05964, dated May 17, 2016.

*Primary Examiner* — Tatyana Zalukaeva
*Assistant Examiner* — Guy K Townsend
(74) *Attorney, Agent, or Firm* — Andrus Intellectual Propert Law, LLP

(57) ABSTRACT

An absorbent article having an elastic film stretchable region in which a stretch rate changes depending on the part, and a method of manufacturing the same. The above problem is solved when a stretchable region being stretchable at least in a width direction is included in a lower-torso region having a waist portion of an outer body of a front body and an outer body of a back body, and in the stretchable region, in a state in which an elastic film is stretched in a stretching and contracting direction at a stretch rate continuously increasing from a crotch side toward a waist opening side, a first sheet layer and a second sheet layer are joined.

15 Claims, 24 Drawing Sheets

(51) Int. Cl.
*A61F 13/494* (2006.01)
*A61F 13/15* (2006.01)
*A61F 13/51* (2006.01)

(52) U.S. Cl.
CPC ............ *A61F 13/49* (2013.01); *A61F 13/496* (2013.01); *A61F 13/49011* (2013.01); *A61F 13/49406* (2013.01); *A61F 13/51* (2013.01); *A61F 2013/49022* (2013.01); *A61F 2013/4948* (2013.01); *A61F 2013/49057* (2013.01); *A61F 2013/49493* (2013.01)

(56) References Cited

U.S. PATENT DOCUMENTS 5,993,964 A * 11/1999 Nakajima ................. D01F 6/30 428/364
5,997,989 A * 12/1999 Gessner .................... D01F 6/46 156/161
6,039,906 A * 3/2000 Sageser ..................... B26F 1/24 264/156
6,248,195 B1 * 6/2001 Schmitz ................ A61F 13/539 156/290
6,319,455 B1 * 11/2001 Kauschke ............... B32B 27/12 264/518
6,488,801 B1 * 12/2002 Bodaghi ................. B32B 5/022 156/167
2002/0016112 A1 2/2002 Curro et al.
2002/0016122 A1 * 2/2002 Curro ...................... B29C 55/18 442/381
2003/0130641 A1 * 7/2003 Richlen ................. A61F 13/496 604/385.01
2005/0027279 A1 * 2/2005 Minato ............. A61F 13/49011 604/387
2006/0172647 A1 * 8/2006 Mehta .................. D04H 1/4391 442/327
2006/0286343 A1 * 12/2006 Curro ...................... B32B 27/12 428/131
2008/0114325 A1 * 5/2008 Edwall .................. A61F 13/505 604/385.24
2008/0161768 A1 7/2008 Baba et al.
2009/0133180 A1 * 5/2009 Morita .................... B29C 55/18 2/79
2010/0051170 A1 * 3/2010 Nakakado ......... A61F 13/15739 156/73.1
2010/0112313 A1 * 5/2010 Nakakado ......... A61F 13/15601 428/198
2010/0222755 A1 * 9/2010 Westwood ................ B32B 5/06 604/358
2015/0083309 A1 * 3/2015 Long ................. B29C 66/83517 156/161
2015/0173955 A1 * 6/2015 Macura ............ A61F 13/15804 493/374
2015/0176750 A1 * 6/2015 Escobar ............ A61F 13/15804 248/646
2015/0283003 A1 * 10/2015 Rosati ................... A61F 13/535 206/526
2016/0129661 A1 * 5/2016 Arora .................... A61F 13/511 428/137
2016/0220422 A1 * 8/2016 Schneider ......... A61F 13/15699
2016/0220423 A1 * 8/2016 Schneider ......... A61F 13/15739
2016/0220424 A1 * 8/2016 Schneider ......... A61F 13/15699
2016/0278986 A1 * 9/2016 Gross ................ A61F 13/51394

FOREIGN PATENT DOCUMENTS

| | | |
|---|---|---|
| JP | 2004532758 | 10/2004 |
| JP | 4987967 | 5/2012 |
| JP | 5292586 | 6/2013 |
| WO | 2003000165 | 1/2003 |
| WO | 2008078610 | 7/2008 |

* cited by examiner (a)

(b)

(a)

←STRETCHING AND CONTRACTING DIRECTION→

(b)

←STRETCHING AND CONTRACTING DIRECTION→

(c)

←STRETCHING AND CONTRACTING DIRECTION→

(a)

(b)

(a)

(b)

(a)

(b)

ABSORBENT ARTICLE AND METHOD FOR PRODUCING SAME

CROSS-REFERENCE TO RELATED APPLICATIONS

This application is the U.S. national stage application of International Application PCT/JP2016/059624, filed Mar. 25, 2016, which international application was published on Oct. 6, 2016, as International Publication WO 2016/158750. The International Application claims priority of Japanese Patent Application No. 2015-070293, filed Mar. 30, 2015. The international application and Japanese application are both incorporated herein by reference, in entirety.

TECHNICAL FIELD

The present invention relates to an absorbent article having an elastic film stretchable structure formed by interposing an elastic film between sheet layers, and a method of manufacturing the same.

BACKGROUND ART

In absorbent articles, elastic characteristics are typically imparted to leg portions, waist portions, and the like to improve fitness to the surfaces of bodies. A typical approach to impart elastic characteristics is fixing of elongated elastically stretchable members, such as rubber threads, in a state stretched in the longitudinal direction. An approach to impart excellent surface fitting is fixing of elastic film in a state stretched in a direction of imparting elasticity (for example, see Patent Literatures 1 to 3).

According to a stretchable structure using the elastic film (hereinafter also referred to as an elastic film stretchable structure), a stretchable region is composed of a first sheet layer, a second sheet layer, and an elastic film interposed therebetween, and the first sheet layer and the second sheet layer are joined via through holes formed in the elastic film or through the elastic film at a large number of bond portions arranged at intervals in a stretching and contracting direction and a direction orthogonal thereto while the elastic film is stretched in the stretching and contracting direction along the surfaces of the first sheet layer and the second sheet layer. In such an elastic film stretchable structure, in a natural length state, as the elastic film contracts between the bond portions, an interval between the two adjacent bond portions is decreased, and a contraction wrinkle extending in the direction orthogonal to the stretching and contracting direction is formed between the bond portions in the first sheet layer and the second sheet layer. On the contrary, in a stretched state, as the elastic film is stretched between the bond portions, the interval between the two adjacent bond portions is increased and the contraction wrinkle in the first sheet layer and the second sheet layer is stretched, and elastic stretching is allowed so that the first sheet layer and the second sheet layer can be completely spread. This elastic film stretchable structure has advantages as follows: surface fitness is excellent; the first sheet layer and the second sheet layer are joined each other at an extremely low level, thus the elastic film stretchable structure has a satisfactory softness; and the through holes of the elastic film contribute to improvement in air permeability.

However, in the stretchable region formed by the conventional elastic film, elasticity does not change in the direction orthogonal to the stretching and contracting direction. For this reason, in order to change elasticity depending on the part, for example, a contraction force applied to a waist portion is made to be larger than that applied to a crotch side. Thus, as exemplified by Patent Literatures 2 and 3, a stretchable region based on an elastic film and a stretchable region based on a rubber thread are individually provided.

Even when a rubber thread is not separately fixed unlike in Patent Literatures 2 and 3, by fixing a plurality of elastic films 30 so as to have different stretch rates, respectively, elasticity of each elastic film may be changed depending on the part. However, when tension is applied to the elastic films 30 to convey the elastic films 30 in a production line, WIDTH-DECREASING is caused in each of the elastic films 30 (a width of the elastic film in the middle in a conveying direction becomes relatively narrow), and thus it is difficult to form a continuous stretchable region using the plurality of elastic films 30.

CITATION LIST

Patent Literature

Patent Literature 1: JP 2004-532758 A
Patent Literature 2: JP 4987967 B2
Patent Literature 3: JP 5292586 B2

SUMMARY OF INVENTION

Technical Problem

In this regard, a main problem of the present invention is to provide an absorbent article including an elastic film stretchable region in which elasticity changes depending on the part and a method of manufacturing the same.

Solution to Problem

The invention solving the above problem is described below.

<Invention Described in Claim 1>

An absorbent article comprising a stretchable region being stretchable at least in one direction, wherein the stretchable region is formed by stacking an elastic film between a first sheet layer made of a nonwoven fabric and a second sheet layer made of a nonwoven fabric, and in a state in which the elastic film is stretched in a stretching and contracting direction of the stretchable region at a stretch rate continuously changing in a direction orthogonal to the stretching and contracting direction, the first sheet layer and the second sheet layer are joined via through holes formed in the elastic film at a large number of bond portions arranged at intervals in the stretching and contracting direction and the direction orthogonal thereto.

(Operational Advantage)

In the stretchable region of the present invention, in a natural length state of the elastic film, an interval between the two adjacent bond portions becomes narrow as the elastic film contracts between the bond portions, and a contraction wrinkle extending in the direction orthogonal to the stretching and contracting direction is formed between the bond portions in the first sheet layer and the second sheet layer. On the contrary, in a stretched state, as the elastic film is stretched between the bond portions, the interval between the two adjacent bond portions becomes wide and the contraction wrinkle in the first sheet layer and the second sheet layer is stretched, and the elastic film is allowed to stretch elastically up to a completely spread state of the first sheet layer and the second sheet layer. Further, in the stretchable region, in the state in which the elastic film is stretched in the stretching and contracting direction at the stretch rate continuously changing in the direction orthogonal to the stretching and contracting direction, the first sheet layer and the second sheet layer are joined together. Thus, while the stretchable region is based on the elastic film, elasticity may be changed depending on the part in the direction orthogonal to the stretching and contracting direction, and more preferable fitness may be obtained.

<Invention Described in Claim 2>

The absorbent article according to claim 1, wherein the absorbent article is an underpants-type disposable diaper comprising an outer body included in a front body and a back body, and an inner body that includes an absorber and is fixed to an internal surface of the outer body, wherein both side portions of the outer body in the front body are respectively joined to both side portions of the outer body in the back body to define side seal portions, and a lower-torso region in an annular shape, a waist opening and a pair of right and left leg openings are thereby formed, at least one of the outer body of the front body and the outer body of the back body has the stretchable region being stretchable at least in a width direction in a portion of the lower-torso region including at least a waist portion, and in the stretchable region, in a state in which the elastic film is stretched in the stretching and contracting direction at the stretch rate continuously increasing from a crotch side toward a waist opening side, the first sheet layer and the second sheet layer are joined together.

(Operational Advantage)

The underpants-type disposable diaper having such a structure is an absorbent article, which is particularly preferable to have an elastic film stretchable structure, since the outer body needs to have elasticity in a wide range and be excellent in air permeability. However, it is required that a stronger contraction force is applied to the waist portion than that applied to the crotch side, and thus, conventionally, a rubber thread needs to be added to the waist portion as in Patent Literatures 2 and 3. On the other hand, in the present invention, elasticity may be changed depending on the part. Thus, as in this claim, for example, when elastic film is allowed to extend up to the waist portion by joining the first sheet layer and the second sheet layer together while stretching the elastic film in the width direction at a stretch rate continuously increasing from the crotch side toward the waist opening side, it is possible to increase a contraction force applied to the waist portion in wearing without providing a separate rubber thread in the waist portion. However, it is of course possible that the separate rubber thread may be provided in the waist portion. In this case, the following advantage is obtained. In a conventional underpants-type disposable diaper in which an elongated elastically stretchable member is provided in a lower torso region including a waist portion, the waist portion should remarkably contract when compared to a part on the crotch side thereof, and thus appearance deteriorates. However, when the elastic film is fixed at the stretch rate continuously changing and the elongated elastically stretchable member of the waist portion is combined with the elastic film fixed in this way, appearance is excellent due to continuous change in the contraction amount.

<Invention Described in Claim 3>

The absorbent article according to claim 1 or 2, wherein an area of each of the bond portions in the stretchable region is in a range of 0.14 to 3.5 $mm^2$, an area of an opening of each of the through holes in a natural length state is 1 to 1.5 times the area of each of the bond portions, an area rate of the bond portions in the stretchable region is in a range of 1.8 to 22.5%, the stretchable region corresponds to a region in which the bond portions are arranged in the same pattern, and a portion having a highest elongation at an elastic limit in the stretchable region has a stretch rate set to 1.1 to 1.5 times the stretch rate of a portion having a lowest elongation at the elastic limit in the stretchable region.

(Operational Advantage)

The area of the bond portion, the area of the opening of the through hole, the area rate of the bond portion, the extent of change of the stretch rate, etc. may be appropriately determined. However, in a normal case, it is desirable to set the values within the above ranges. Here, the "area rate" refers to the proportion of a target portion per unit area, and expresses the proportion in percentage by dividing a total area of the target portion (for example, the bond portions and the openings of the through holes) in a target region (for example, the stretchable region) by an area of the target region. Particularly, the "area rate of the bond portions" refers to an area rate in a state of being stretched in the stretching and contracting direction up to the elastic limit. In addition, the area of the opening of the through hole refers to a value in a state in which the stretchable structure is in a natural length state. When the area of the opening of the through hole is not uniform in the thickness direction, for example, when the area is different between a front and aback of the elastic film, the area refers to a minimum value. In addition, the "elongation at the elastic limit" refers to the proportion of the length in percentage at an elastic limit (in other words, in a state in which the first sheet layer and the second sheet layer are completely spread)-relative to the natural length set to 100%.

<Invention Described in Claim 4>

A method of manufacturing an absorbent article including a stretchable region being stretchable at least in one direction, wherein in forming the stretchable region, in a state in which an elastic film is interposed between a first sheet layer made of a nonwoven fabric and a second sheet layer made of a nonwoven fabric while being stretched in a stretching and contracting direction of the stretchable region at a stretch rate continuously changing in a direction orthogonal to the stretching and contracting direction, the elastic film is melted to form through holes at a large number of positions arranged at intervals in the stretching and contracting direction and the direction orthogonal thereto, and the first sheet layer and the second sheet layer are joined via the through holes.

(Operational Advantage)

According to such a manufacturing method, while the stretchable region is based on the elastic film, elasticity may be changed depending on the part in the direction orthogonal to the stretching and contracting direction, and an absorbent article having more preferable fitness may be manufactured.

Advantageous Effects of Invention

As described above, the present invention has an advantage that an absorbent article including an elastic film stretchable region in which elasticity changes depending on the part and a method of manufacturing the same and the like are obtained.

DESCRIPTION OF EMBODIMENTS

Figure 1:
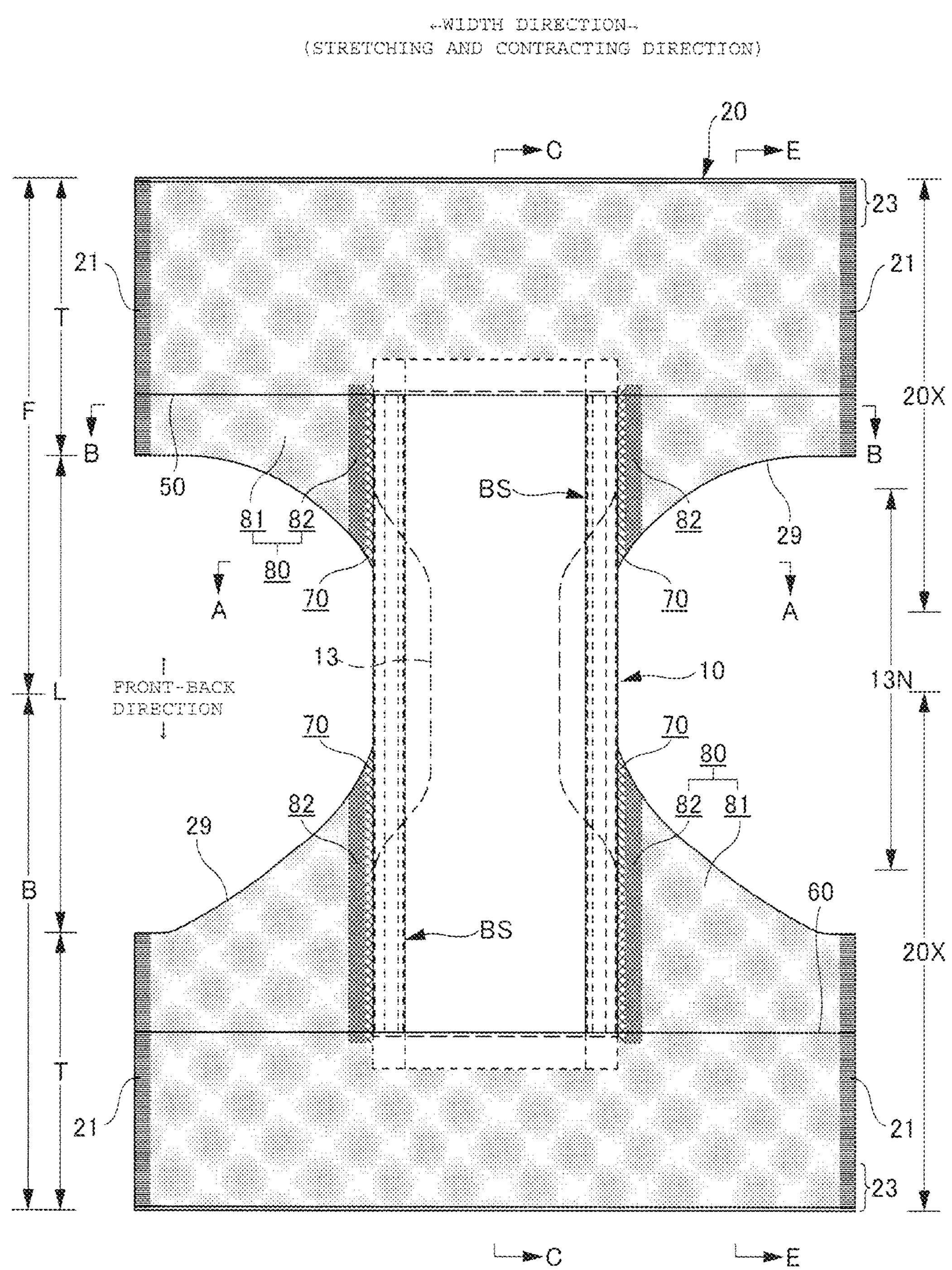
FIG. 1 is a plan view (internal surface side) of an underpants-type disposable diaper in a completely spread state.

Hereinafter, an embodiment of the invention will be described with reference to accompanying drawings. A dotted portion in a cross-sectional view indicates joining means such as a hot-melt adhesive.

FIG. 1 to FIG. 7 illustrate an underpants-type disposable diaper. This underpants-type disposable diaper (hereinafter also simply referred to as a diaper) has an outer body 20 included in a front body F and a back body B, and an inner body 10 that is fixed in a unified manner to the internal surface of the outer body 20. Further, in the inner body 10, an absorber 13 is interposed between a liquid pervious front surface sheet 11 and a liquid impervious back surface side sheet 12. In manufacturing, after a back surface of the inner body 10 is joined to the internal surface (upper surface) of the outer body 20 using joining means such as a hot-melt adhesive (a shaded part 10B of FIG. 7), the inner body 10 and the outer body 20 are folded at a boundary between the front body F and the back body B, i.e., in the center in the front-back direction or longitudinal direction, and both side portions thereof are joined to each other by heat sealing, a hot-melt adhesive, etc. to form side seal portions 21, thereby obtaining an underpants-type disposable diaper in which a waist opening and a pair of right and left leg openings are formed.

(Exemplary Structure of Inner Body)

Figure 4:
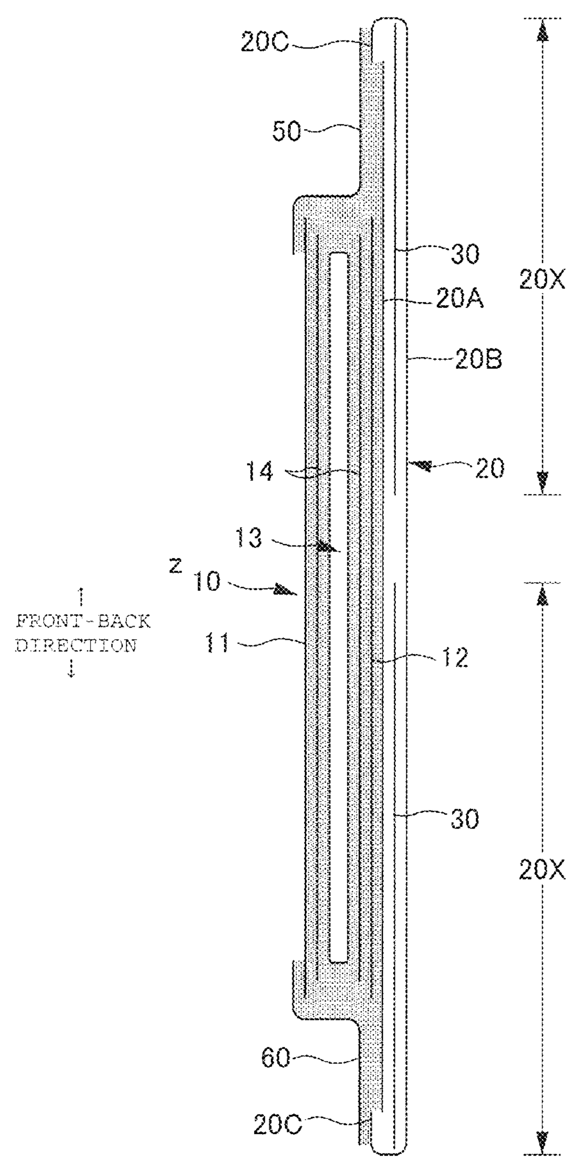
FIG. 4(*a*) is a C-C cross-sectional view of FIG. 1, and FIG. 4(*b*) is an E-E cross-sectional view of FIG. 1.
Figure 4:
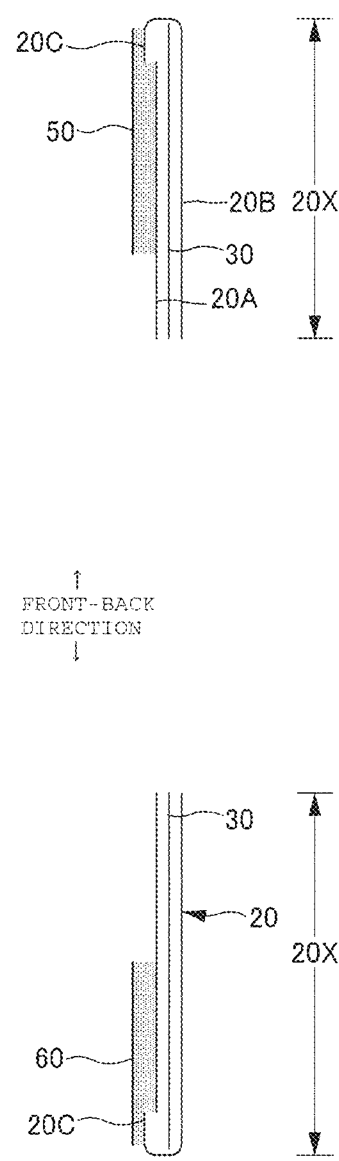
Figure 5:
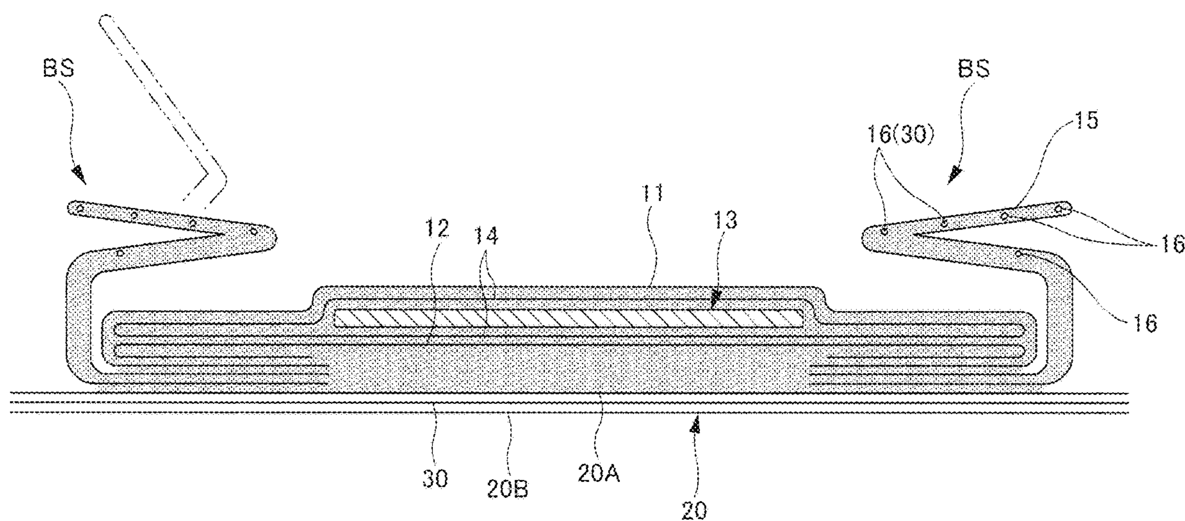
FIG. 5 is an A-A cross-sectional view of FIG. 1.
Figure 6:
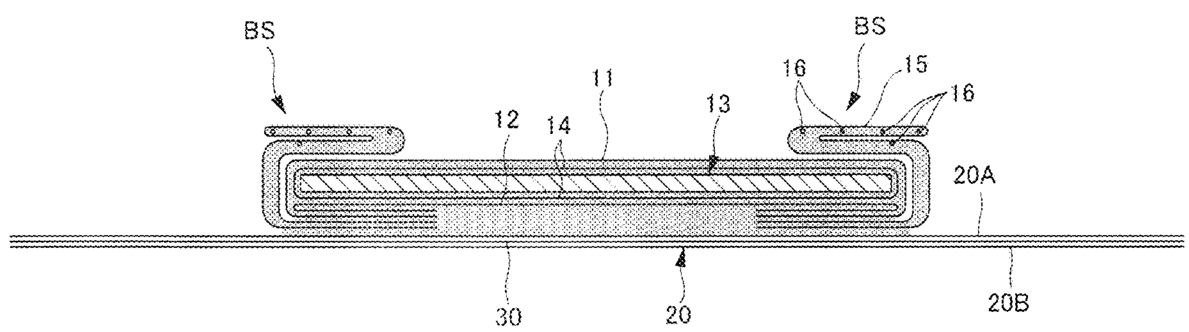
FIG. 6 is a B-B cross-sectional view of FIG. 1.
Figure 7:
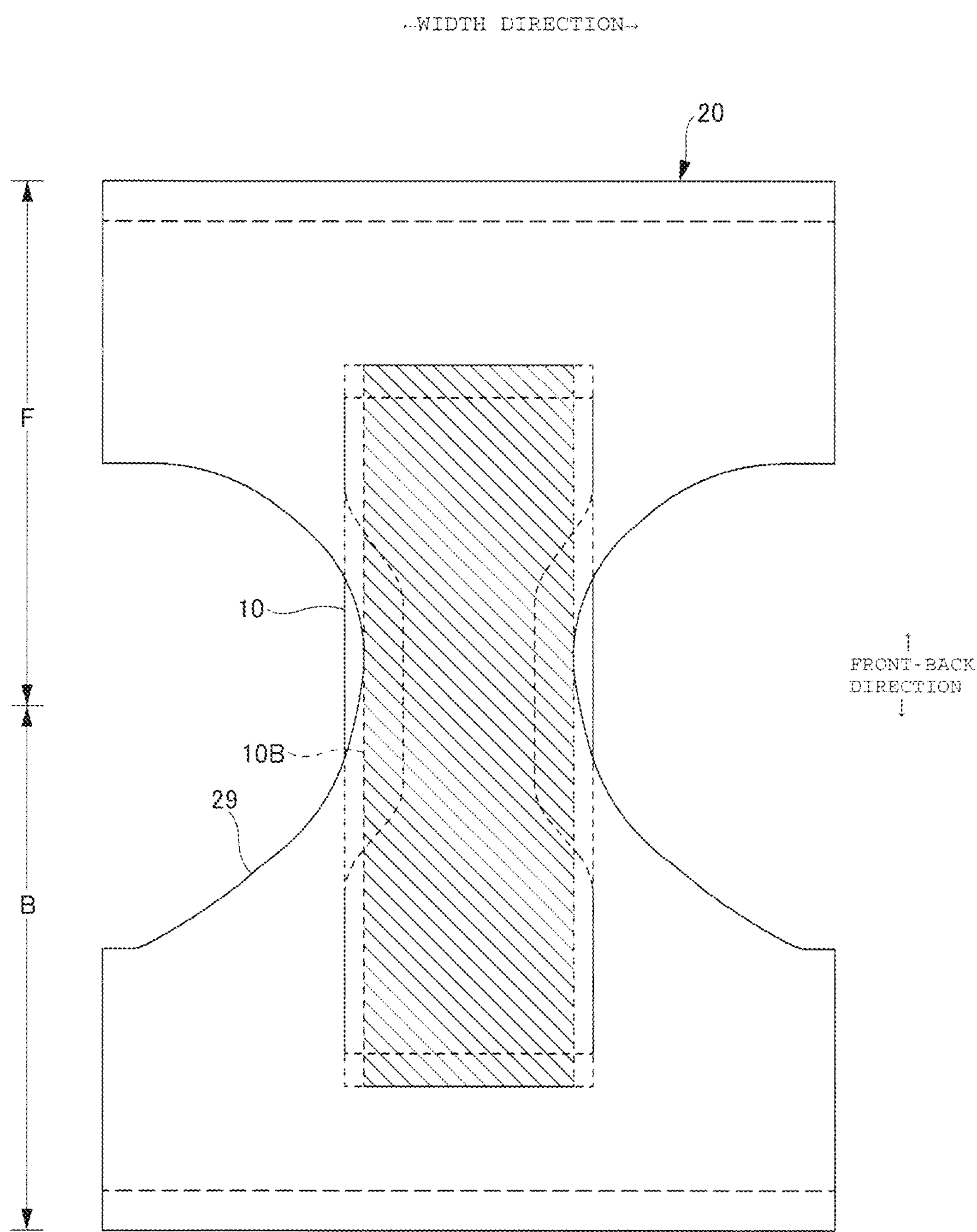
FIG. 7 is a plan view illustrating only a main part of the underpants-type disposable diaper in the completely spread state.

With reference to FIGS. 4 to 6, the inner body 10 includes a liquid-pervious front surface sheet 11 composed of, for example, non-woven fabric, a liquid-impermeable back surface side sheet 12 composed of, for example, polyethylene, and an absorber 13 interposed between the front surface sheet 11 and the liquid-impermeable back surface side sheet 12. The inner body 10 is configured to absorb and retain excretory fluid passing through the front surface sheet 11. The inner body 10 may have any planar shape and typically has a substantially rectangular shape as shown in the drawing.

The liquid-pervious front surface sheet 11 that covers a front surface side (skin-contacting side) of the absorber 13 is preferably composed of perforated or imperforate nonwoven fabric or a porous plastic sheet. Examples of the raw fibers of the nonwoven fabric include synthetic fibers, such as olefin fibers, e.g., polyethylene and polypropylene, polyester fibers, and polyamide fibers; recycled fibers, such as rayon and cupra; and natural fibers, such as cotton. The nonwoven fabric can be produced by any process, for example, spun lacing, spun bonding, thermal bonding, melt blowing, or needle punching. Among these processes, preferred are spun lacing in view of softness and drape characteristics and thermal bonding in view of bulky soft products. A large number of through holes formed in the liquid-pervious front surface sheet 11 facilitates absorption of urine and achieves dry touch characteristics. The liquid-pervious front surface sheet 11 extends around the side edges of the absorber 13 and extends to the back surface side of the absorber 13.

The liquid-impermeable back surface side sheet 12, covering the back surface side (non-skin-contacting side) of the absorber 13 is composed of a liquid-impervious plastic sheet, for example, polyethylene sheet or polypropylene sheet. Recently, permeable films have been preferably used in view of preventing stuffiness. This water-block permeable sheet is a micro-porous sheet prepared through melt-kneading an olefin resin, for example, polyethylene resin or polypropylene resin, and inorganic filler, forming a sheet with the kneaded materials, and then uniaxially or biaxially elongating the sheet.

The absorber 13 may be composed of a well-known basic component, such as an accumulated body of pulp fibers, an assembly of filaments, composed of, for example, cellulose acetate, or nonwoven fabric, and the absorber 13 may include as necessary high-absorbent polymer mixed or fixed to the basic component. The absorber 13 may be wrapped with a liquid-permeable and liquid-retainable package sheet 14, such as a crepe sheet, to retain the shape and polymers, as required.

The absorber 13 has a substantially hourglass shape having a narrower portion 13N with a width narrower than those of the front and back end portions of the absorber 13, at a crotch portion. Alternatively, the absorber 13 may have any other shape, for example, a rectangular shape, as appropriate. The size of the narrower portion 13N may be appropriately determined. The narrower portion 13N may have a length of approximately 20 to 50% of the entire length of the diaper along the front-back direction, and a width, at the narrowest region, of approximately 40 to 60% of the entire width of the absorber 13. If the inner body 10 has a substantially rectangular planar shape in the case of the absorber with such a narrower portion 13N, the inner body 10 has portions free of the absorber 13 according to the narrower portion 13N of the absorber 13.

Three-dimensional gathers BS, which are configured to fit around the legs, are formed on both side portions of the inner body 10. With reference to FIGS. 5 and 6, the three-dimensional gathers BS are each composed of a gather nonwoven fabric 15 folded into a duplicate sheet consisting of a fixed section fixed to the side portion of the back surface of the inner body, a main section extending from the fixed section around the side portion of the inner body to the side portion of the front surface of the inner body, lying down sections formed by fixing the front end portion and back end portion of the main section in a lying down state to the side portion of the front surface of the inner body, and a free section formed in an un-fixed state between the lying down sections.

Elongated gather elastic members 16 are disposed in each duplicate sheet, for example, at the tip portion of the free section. As illustrated by the chain double-dashed line in FIG. 5, the free section of the gather elastic members 16 is erected by elastic stretching force to form the three-dimensional gather BS in a completed product.

The liquid impervious back surface side sheet 12 is folded back to the back surface side together with the liquid-pervious front surface sheet 11 at both sides of the absorber 13 in the width direction. The liquid-impervious back surface side sheet 12 is preferably opaque to block transmission of brown color of stool and urine. Preferred examples of the opacifying agent compounded in the plastic film include colorant or filler, such as calcium carbonate, titanium oxide, zinc oxide, white carbon, clay, talc, and barium sulfate.

The gather elastic member 16 may be composed of commodity materials, for example, styrene rubber, olefin rubber, urethane rubber, ester rubber, polyurethanes, polyethylene, polystyrene, styrene-butadiene, silicones, and polyester. The gather elastic members 16 preferably have a fineness of 925 dtex or less and are disposed under a tension of 150% to 350% at an interval of 7.0 mm or less to be hidden from outside view. The gather elastic member 16 may have a string shape shown in the drawing or a tape shape with an appropriate width.

Like the liquid-pervious front surface sheet 11, the gather nonwoven fabric 15 may be composed of raw fibers including synthetic fibers, such as olefin fibers of, for example, polyethylene fibers or polypropylene fibers; polyester fibers and amide fibers; recycled fibers of, for example, rayon and cupra; and natural fibers such as cotton. The gather nonwoven fabric may be prepared by any appropriate process, for example, spun bonding, thermal bonding, melt blowing, or needle punching. In particular, the basis weight should be reduced for production of a nonwoven fabric that can prevent stuffiness and has high air permeability. The gather nonwoven fabric 15 is preferably a water-repellent nonwoven fabric coated with a water repellent agent, for example, a silicone-based agent, a paraffin-metallic agent, or an alkyl chromic chloride agent to decrease permeability of urine and the like, to prevent diaper rash, and to enhance feeling to skin (dryness).

(Structure Example of Outer Body)

In the outer body 20, as illustrated in FIG. 4 to FIG. 6, the elastic film 30 is arranged between the first sheet layer 20A and the second sheet layer 20B, and elasticity in the width direction is imparted. In the illustrated embodiment, a portion located so as to correspond to the waist portion 23 in the elastic film 30 is interposed in the folded part 20C formed by folding back a sheet member of the second sheet layer 20B to the internal surface side at a waist opening edge. However, the portion located so as to correspond to the waist portion 23 may be interposed between a sheet member of the first sheet layer 20A and the sheet member of the second sheet layer 20B. A planar shape of the outer body 20 corresponds to a pseudo-hourglass shape as a whole due to concave leg lines 29 formed as leg openings at both side portions and at the middle of the outer body 20. The outer body 20 may be divided into two front and back parts, and the both parts may be separated from each other in the front-back direction by the crotch portion.

The first sheet layer 20A and the second sheet layer 20B may be composed of any sheet members, preferably nonwoven fabrics in view of air permeability and softness. The nonwoven fabric may be composed of any raw fiber. Examples of the raw fiber include synthetic fibers, such as olefin fibers, e.g., polyethylene fibers and polypropylene fibers, polyester fibers, and polyamide fibers; recycled fibers, such as rayon and cupra; natural fibers, such as cotton; and blend or conjugate fibers composed of two or more of these fibers. The nonwoven fabric may be prepared by any process. Examples of such a process include well-known processes, such as spun lacing, spun bonding, thermal bonding, melt blowing, needle punching, air-through processes, and point bonding. The nonwoven fabric preferably has a basis weight of approximately 10 to 25 g/m$^2$. The first sheet layer 20A and the second sheet layer 20B may be composed of a pair of facing layers prepared by folding back a single sheet that is partially or entirely folded back.

Figure 2:
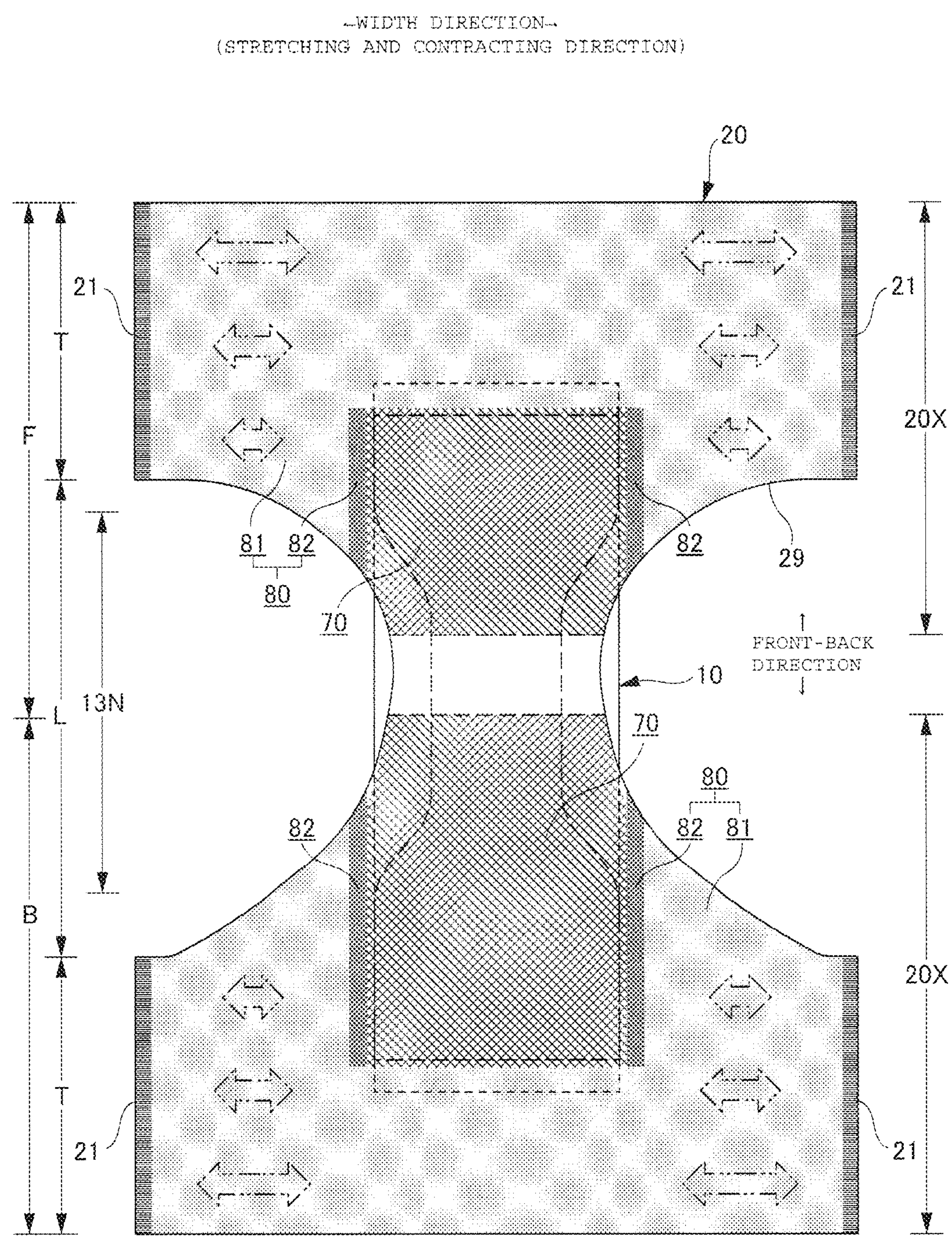
FIG. 2 is a plan view (external surface side) of the underpants-type disposable diaper in the completely spread state.
Figure 3:
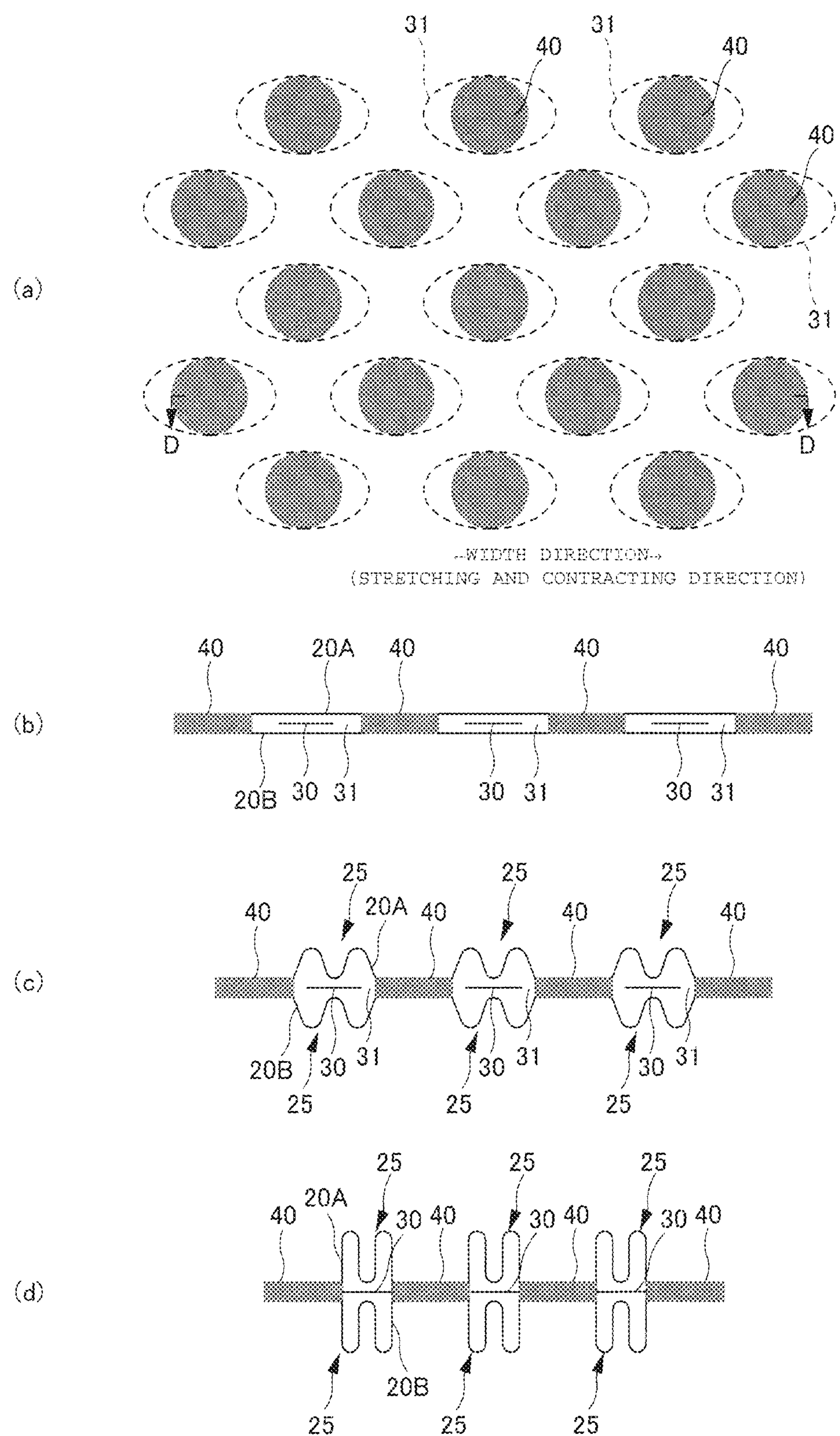
FIG. 3(*a*) is a plan view of a main part of an outer body, FIG. 3(*b*) is a D-D cross-sectional view of FIG. 3(*a*), FIG. 3(*c*) is a cross-sectional view in a worn state, and FIG. 3(*d*) is a cross-sectional view in a natural length state.

In this embodiment, as shown in FIG. 2, the elastic film stretchable structures 20X are formed in the lower-torso region T of the front body F, the lower-torso region T of the back body B, and an intermediate region L therebetween in the outer body 20. That is, in the stretchable structures 20X of the outer body 20, a non-stretchable region 70 is formed in an intermediate portion in the width direction, which includes parts of the outer body 20 overlapping with the absorber 13 (the non-stretchable region 70 may entirely or partly overlap with the absorber 13 and preferably should contain the substantially entire fixed portion 10B of the inner body) as well as the stretchable regions 80 extend to the side seal portions 21 in the width direction. The elastic film 30 is, as shown in FIG. 3, stacked between the first sheet layer 20A and the second sheet layer 20B over the entire stretchable regions 80 and the non-stretchable region 70, and the first sheet layer 20A and second sheet layer 20B are joined at a large number of bond portions 40 arrayed in the stretching and contracting direction and the perpendicular direction thereto at predetermined intervals via the through holes 31 formed in the elastic film 30 in a state in which the elastic film 30 is stretched in the width direction. In this case, it is desirable that the first sheet layer 20A is not and the second sheet layer 20B is not joined to the elastic film 30 (except for a melted and solidified material described below). However, joining is allowed.

Basically, as the area rate of the bond portions 40 increases in the elastic film stretchable structure 20X, portions contracted by the elastic film 30, of the first sheet layer 20A and the second sheet layer 20B, decrease, and the elongation at the elastic limit is likely to decrease. Accordingly, the area rate of the openings of the through holes 31 in the elastic film 30 increases, and thus the proportion of the elastic film 30 continuing in the stretching and contracting direction decreases in a direction orthogonal to the stretching and contracting direction. Accordingly, the contraction force to be generated, in stretching, decreases, and the risk of rupture of the elastic film 30 increases. In view of such characteristics, the area rate of the bond portions 40 in the non-stretchable region 70 is determined to be larger than that in the stretchable regions 80, such that the elongation at the elastic limit in the stretching and contracting direction is 130% or less (preferably 120% or less, more preferably 100%). In contrast, the area rate of the bond portions 40 in the stretchable regions 80 is determined to be smaller than that in the non-stretchable region 70, such that the elongation at the elastic limit in the stretching and contracting direction is 200% or higher (preferably 265 to 295%).

In the stretchable region 80, as illustrated in FIG. 3(*d*), when the elastic film 30 is in the natural length state, the first sheet layer 20A and the second sheet layer 20B between the bond portions are raised in a direction away from each other, and thus a contraction wrinkles 25 extending in a direction intersecting the stretching and contracting direction is formed. In a worn state in which the elastic film 30 is stretched to an extent in the width direction, as illustrated in FIG. 3(*c*), the contraction wrinkles 25 are still remain although the contraction wrinkles 25 are stretched. In addition, as in the illustrated embodiment, in a case that the first sheet layer 20A is not and the second sheet layer 20B is not joined to the elastic film 30 in a portion other than between the first sheet layer 20A and the second sheet layer 20B in the bond portions 40 in the non-stretchable region 70, as understood from FIG. 3(*c*) assuming the worn state and FIGS. 3(*a*) and 3(*b*) assuming a completely spread state of the first sheet layer 20A and the second sheet layer 20B, a gap is formed between the through hole 31 of each of the bond portions in the elastic film 30 and each of the bond portions 40 in these states, and thus air permeability is imparted due to the gap even when a material of the elastic film 30 is a non-porous film or a non-porous sheet. States of the contraction wrinkles 25 in the worn state and the natural length state are shown in sample photographs of FIGS. 12 to 14.

Figure 12:
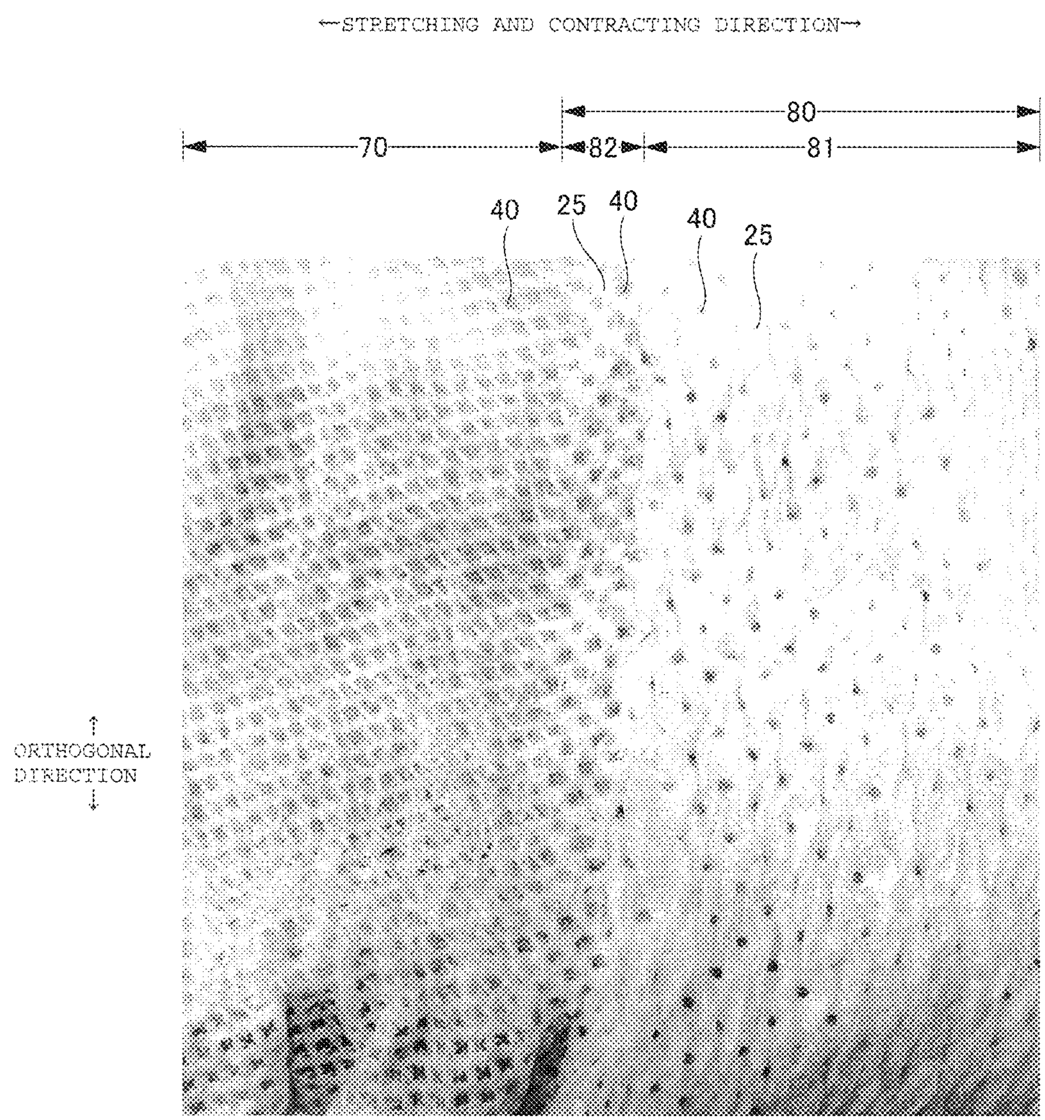
FIG. 12 is a photograph in a natural length state of a sample of an embodiment.
Figure 13:
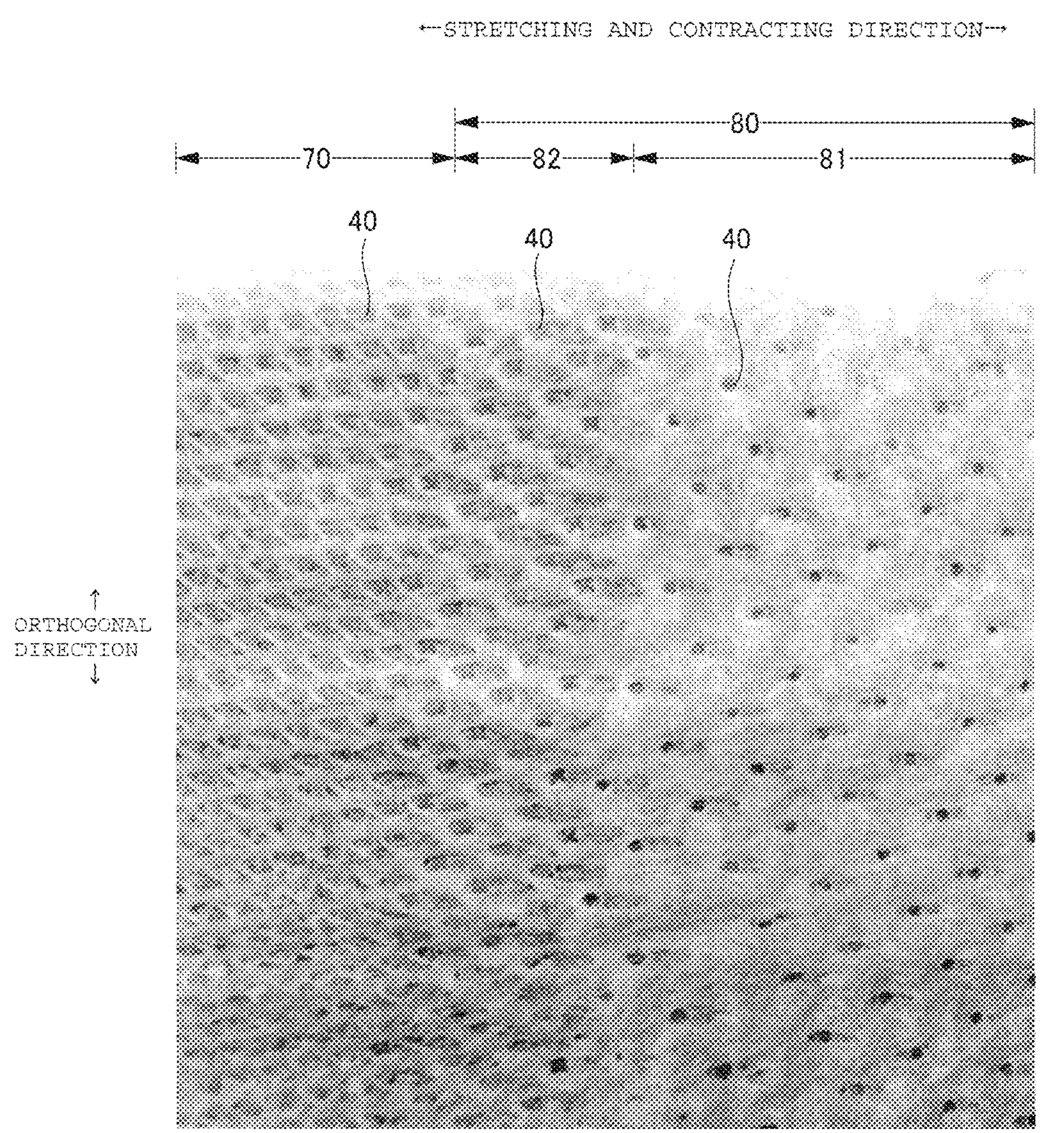
FIG. 13 is a photograph in a stretched state of a sample of an embodiment.
Figure 14:
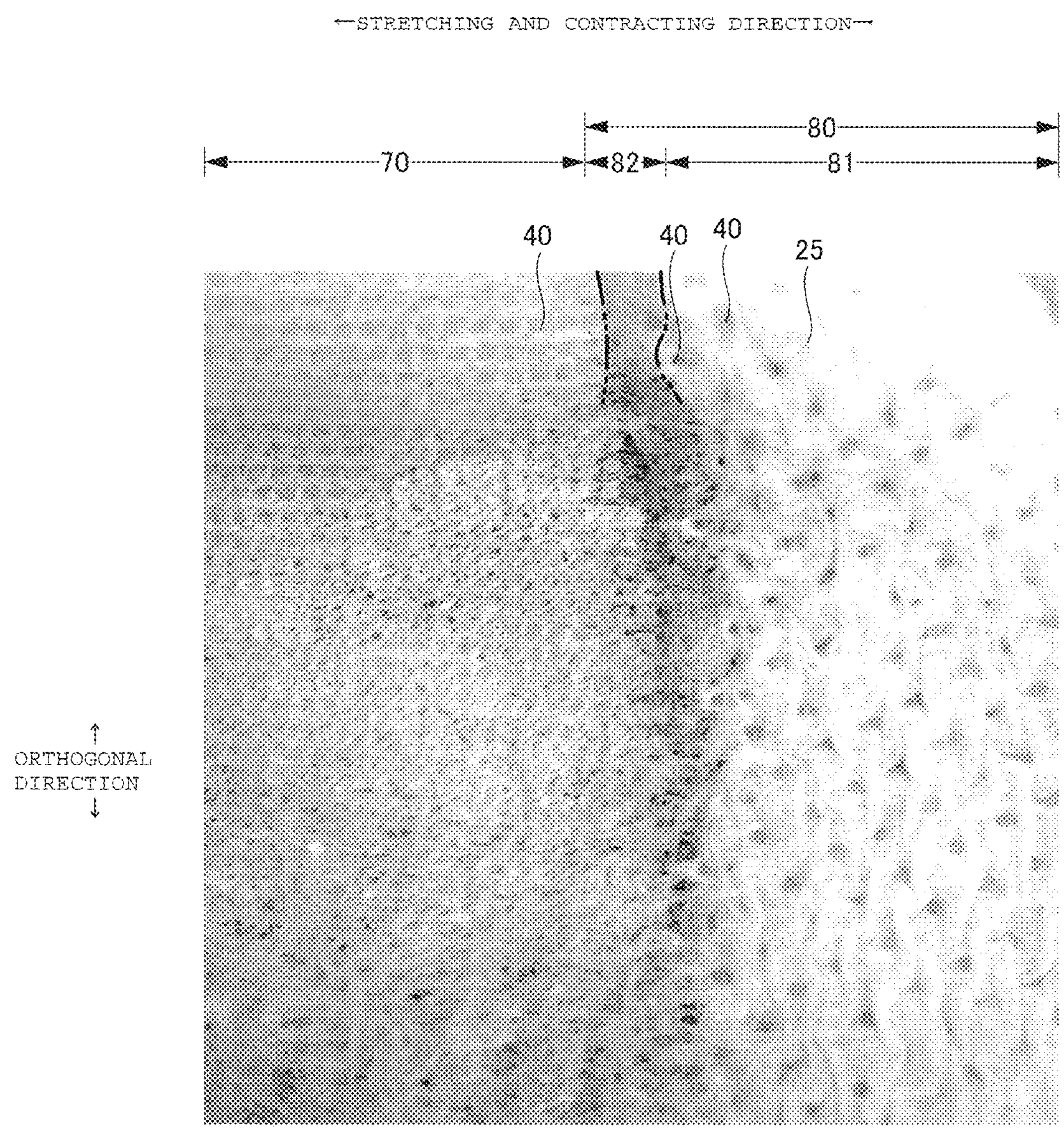
FIG. 14 is a photograph illustrating a natural length state after an elastic film is fractured.

In the non-stretchable region 70, as understood from the sample photographs of FIGS. 12 to 14, a raised portion or an extremely fine wrinkle is formed between the bond portions 40. However, since the area rate of the bond portions 40 is significantly high, elasticity is substantially eliminated.

Figure 9:
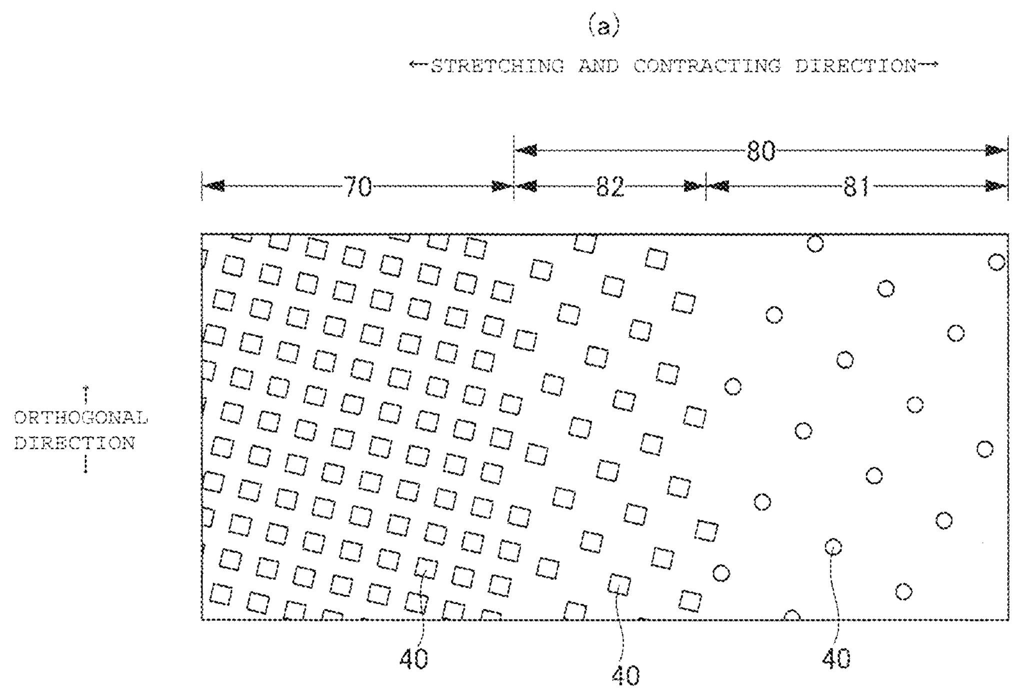
FIG. 9 is a schematic plan view of a main part of the outer body in the completely spread state.
Figure 9:
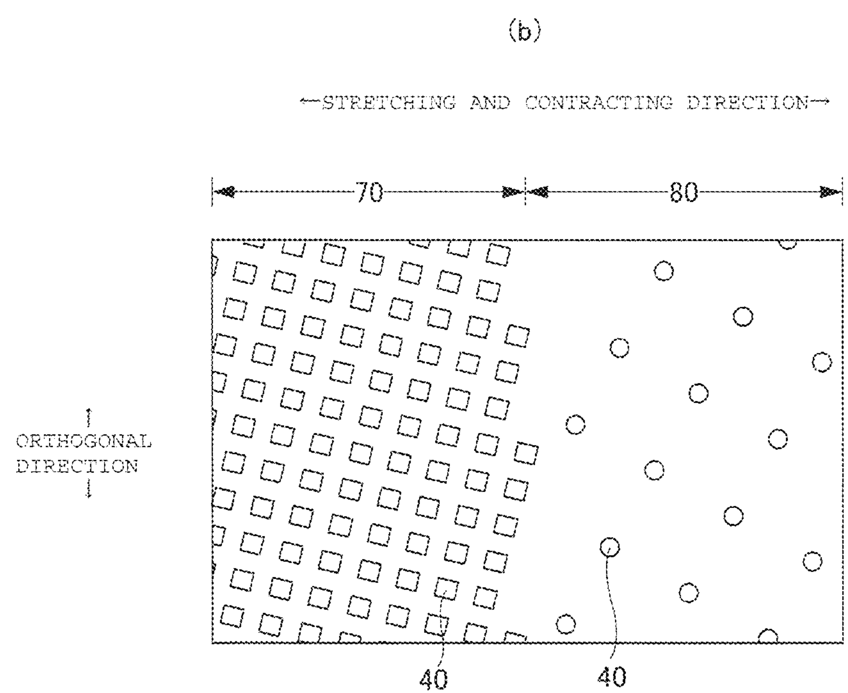

In this embodiment, with reference to FIGS. 2 and 9(*a*), ends of the stretchable regions 80 adjacent to the non-stretchable regions 70 are set to buffer stretchable sections 82 each having a smaller area rate of the bond portions 40 than that of the remaining sections or main stretchable sections 81 of the stretchable regions 80. When stretched, the buffer stretchable sections 82 are assumed to cause the following variations: In the case where the buffer stretchable sections 82 and the main stretchable sections 81 are stretched from the natural length state by gradually increasing stress, there are the first phase and the second phase. In the first phase, while both of the buffer stretchable sections 82 and the main stretchable sections 81 are stretched, the buffer stretchable sections 82 are stretched to the elastic limit into a completely spread state (illustrated in FIG. 3(*b*)) earlier than the main stretchable sections 81 and the main stretchable sections 81 are in an incompletely spread state (illustrated in FIG. 3(*c*)). The main stretchable sections 81 go through the first phase and then the second phase where the main stretchable sections 81 are stretched to the elastic limit into a completely spread state (illustrated in FIG. 3(*b*)). In the first phase, the buffer stretchable sections 82 having a low elongation at elastic limit are stretched; therefore, a small tension is applied to boundaries between the buffer stretchable sections 82 and the non-stretchable regions 70 of the elastic film 30. Ruptures of the elastic film 30 at the boundaries between the buffer stretchable sections 82 and the non-stretchable regions 70 are thereby prevented. In the second phase, until the main stretchable sections are in a completely spread state, tension corresponding to the elongation of the main stretchable sections 81 is applied to the main stretchable sections 81, the buffer stretchable sections 82, and the non-stretchable regions 70; however, since the buffer stretchable sections 82 cannot be stretched any more after the first phase, and tension applied to the non-stretchable regions 70 and the buffer stretchable sections 82 is entirely supported by the first sheet layer 20A and the second sheet layer 20B. As a result, the tension applied to the boundaries between the buffer stretchable sections 82 and the non-stretchable regions 70 of the elastic film 30 does not exceed the elongation at elastic limit in the first phase. Ruptures of the elastic film 30 along the boundaries between the buffer stretchable sections 82 and the non-stretchable regions 70 are thereby prevented, as in the first phase.

In contrast, although it is possible that buffer stretchable sections 82 are not provided as illustrated in FIG. 9(*b*), in such a case, the stretchable region 80 has a high elongation at an elastic limit, and tension applied to the boundary between the stretchable region 80 and the non-stretchable region 70 of the elastic film 30 increases until the boundary between the stretchable region 80 and the non-stretchable region 70 of the elastic film 30 is stretched to the elongation at elastic limit into a completely spread state. The elastic film 30 is thereby likely to rupture along the boundary between the stretchable region 80 and the non-stretchable region 70 (the edges of the ruptured elastic film is indicated by the chain double-dashed lines), as illustrated in FIG. 14.

In view of the principle described above, it is preferred that the elongation at elastic limit of the buffer stretchable section 82 be smaller than a tensile elongation in the stretching and contracting direction of the elastic film 30 having a width equal to an interval between two adjacent through holes 31 formed in the elastic film 30 and arrayed in the direction orthogonal to the stretching and contracting direction and in the non-stretchable region 70, to certainly prevent the rupture of the elastic film 30 at the boundary between the stretchable region 80 and the non-stretchable region 70.

A shape of each of the bond portions 40 and of each of the through holes 31 in the natural length state may be set to an arbitrary shape such as a perfect circle, an ellipse, a polygon such as a rectangle (including a linear shape or a rounded corner), a star shape, a cloud shape, etc. A size of each of the bond portions 40 may be appropriately determined. At an excessively large size, the hardness of the bond portions 40 significantly affects the touch, whereas at an excessively small size, the bonded area is too small to certainly bond the layers. Each of the bond portions 40 preferably has an area of approximately 0.14 to 3.5 $mm^2$, in usual cases. Each of the through holes 31 should have an opening area larger than that of the corresponding bond portion 40 when the bond portion 40 is formed and joined within the through hole 31. The through hole 31 preferably has an opening area of approximately 1 to 1.5 times the area of the bond portion 40.

In general, the area and the area rate of each of the bond portions 40 in each region are preferably set as below.

(Non-Stretchable Region 70)

Area of each of bond portions 40: 0.14 to 3.5 $mm^2$ (particularly 0.25 to 1.0 $mm^2$)

Area rate of bond portions 40: 16 to 45% (particularly 25 to 45%)

(Main Stretchable Section 81)

Area of each of bond portions 40: 0.14 to 3.5 $mm^2$ (particularly 0.14 to 1.0 $mm^2$)

Area rate of bond portions 40: 1.8 to 19.1% (particularly 1.8 to 10.6%)

(Buffer Stretchable Section 82)

Area of each of bond portions 40: 0.14 to 3.5 $mm^2$ (particularly 0.25 to 1.0 $mm^2$)

Area rate of bond portions 40: 8 to 22.5% (particularly 12.5 to 22.5%)

Figure 10:
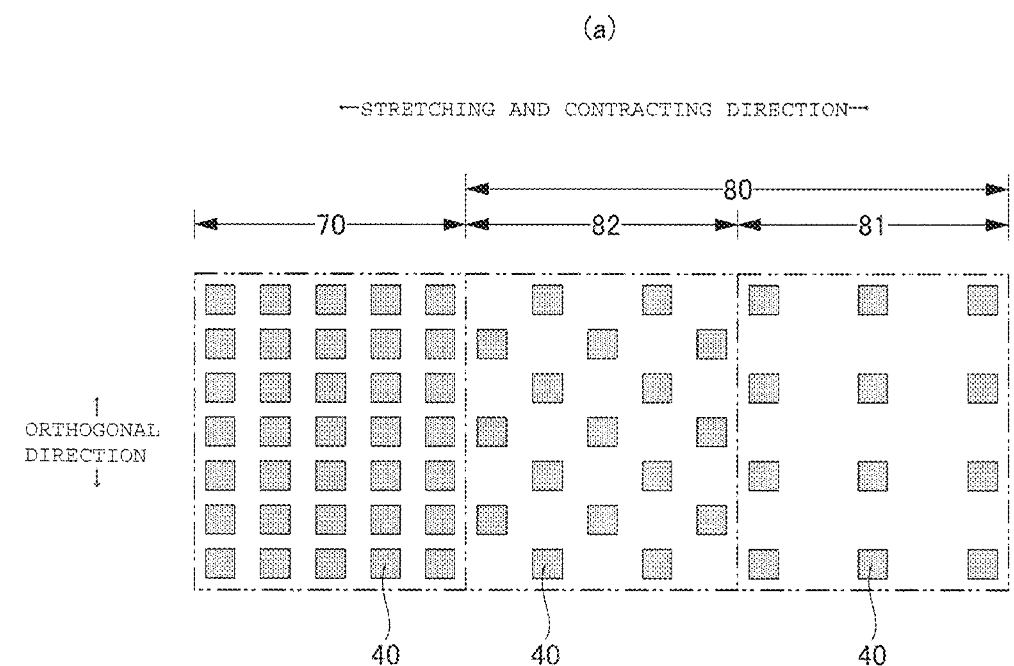
FIG. 10 is an enlarged plan view of a main part illustrating a pattern of bond portions.
Figure 10:
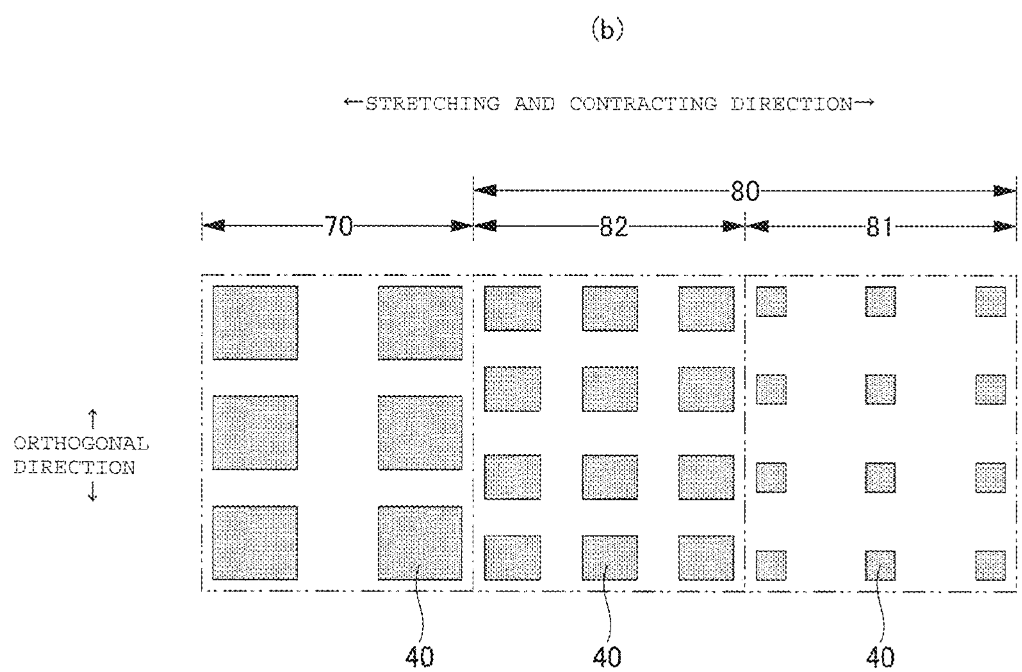

To produce three fields (i.e., the non-stretchable region 70, the main stretchable section 81, and the buffer stretchable section 82) having different area rates, the number of the bond portions 40 per unit area may be varied, as illustrated in FIG. 10(*a*), or the area of each of the bond portions 40 may be varied, as illustrated in FIG. 10(*b*). In the former case, the areas of the bond portions 40 may be the same between two or more fields of the non-stretchable region 70, the main stretchable section 81, and the buffer stretchable section 82, or may be different among all the fields. In the latter case, the number of the bond portions 40 per unit area may the same between two or more fields of the non-stretchable region 70, the main stretchable section 81, and the buffer stretchable section 82, or may be different among all the fields.

Figure 15:
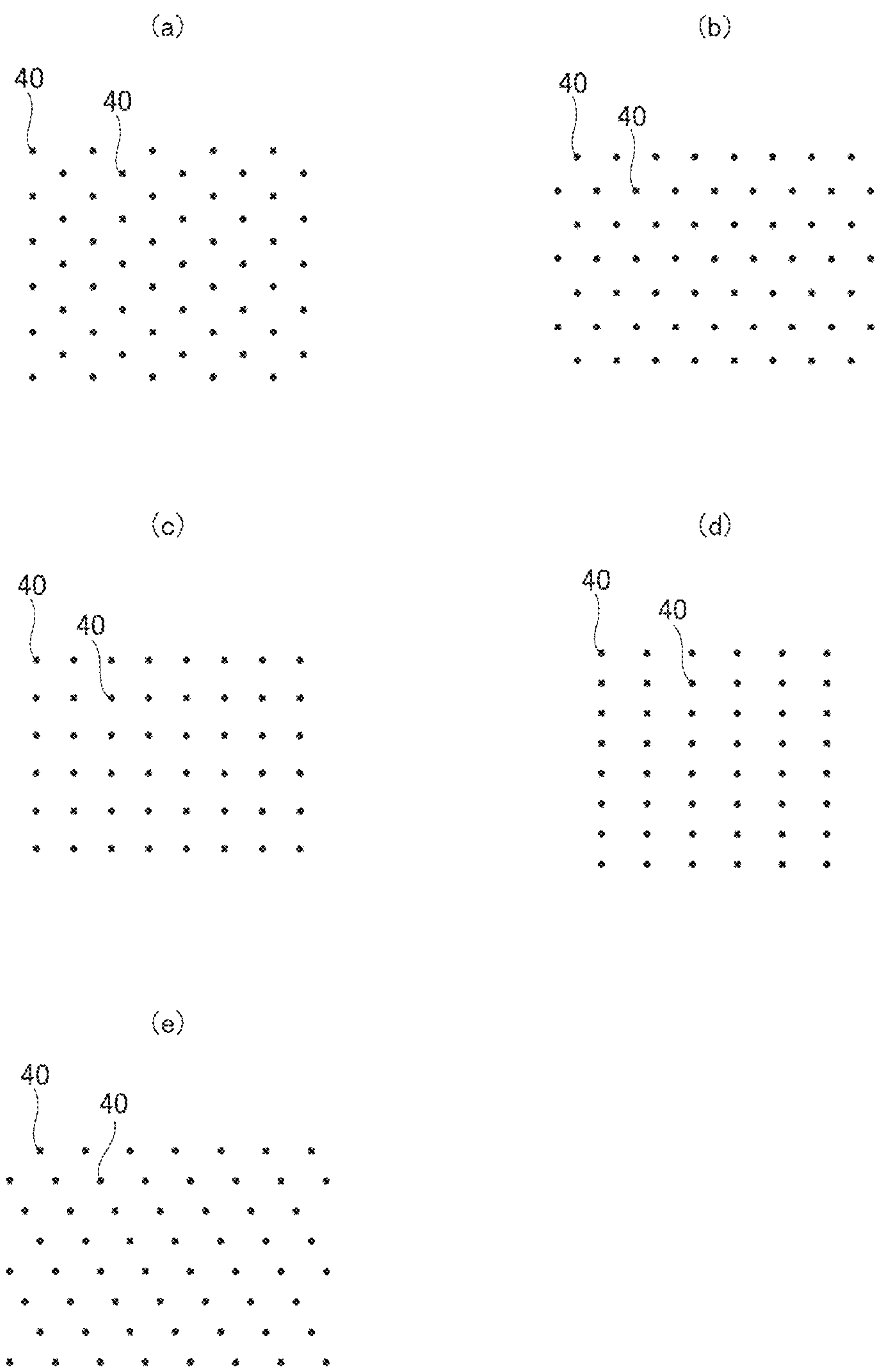
FIG. 15 is a plan view illustrating various arrangement examples of the bond portions.

The planar geometries of the bond portions 40 and the through holes 31 may be appropriately determined. Preferred is regularly repeated geometry, such as an oblique lattice illustrated in FIG. 15(*a*), hexagonal lattice (also referred to as staggered lattice) illustrated in FIG. 15(*b*), square lattice illustrated in FIG. 15(*c*), rectangular lattice illustrated in FIG. 15(*d*), or parallelotope lattice illustrated in FIG. 15(*e*) (where two groups of a large number of diagonally parallel arrays intersect each other, as shown in the drawings) (including arrays tilted by less than 90 degrees to the stretching and contracting direction). Alternatively, the bond portions 40 may be arrayed in regularly repeated groups (the geometry of each group may be regular or irregular, in other words, may be in a pattern or characteristic letters, for example). The geometries of the bond portions 40 and the through holes 31 may be the same or different among the main stretchable section 81, the buffer stretchable section 82, and the non-stretchable region 70.

Figure 11:
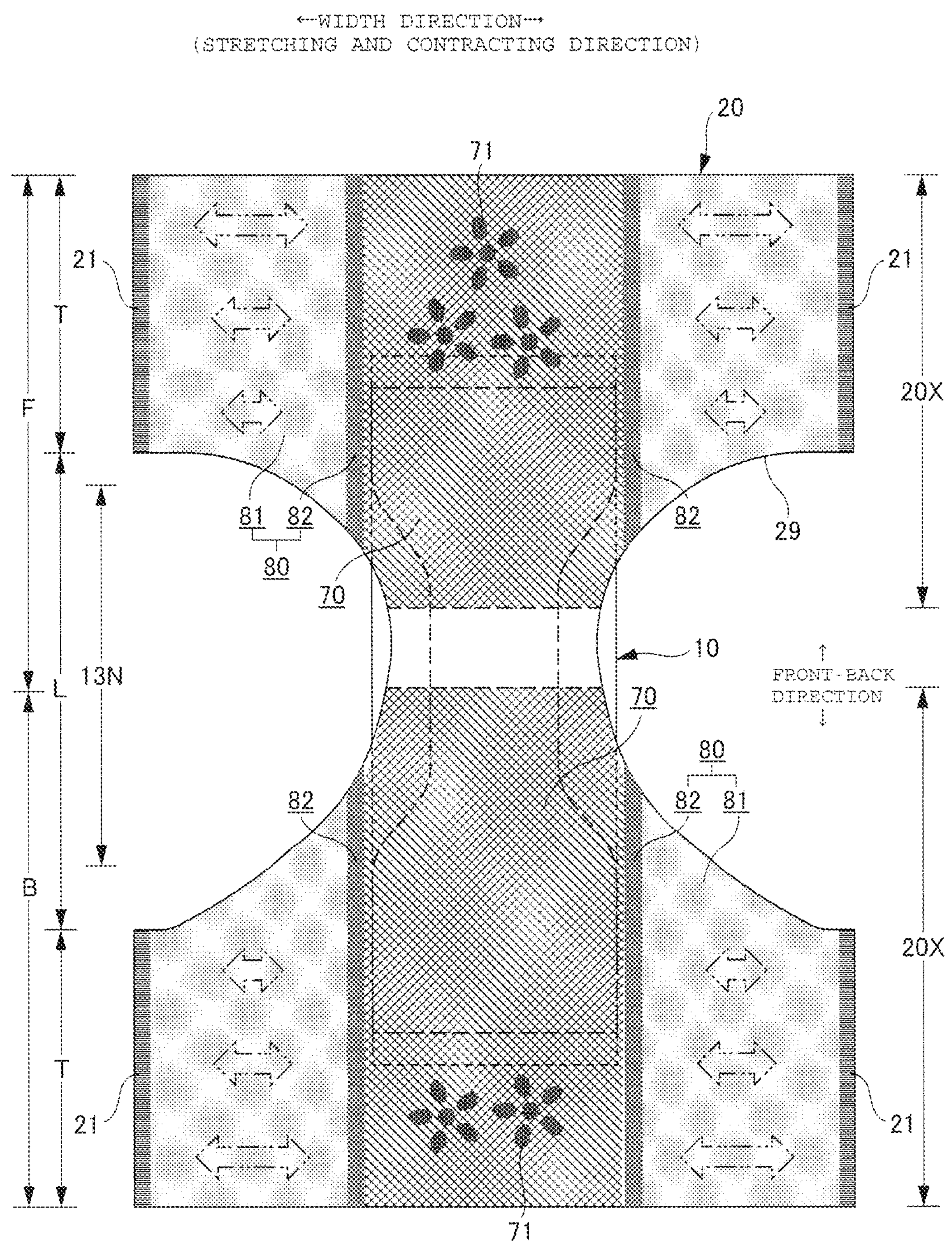
FIG. 11 is a plan view (external surface side) of an underpants-type disposable diaper in a completely spread state.

As illustrated in FIG. 11, in addition to the portion overlapping with the absorber 13, for example, it is possible to provide the non-stretchable region 70 in which the bond portions 40 are disposed in a shape of an indication 71. In this case, the buffer stretchable section may be provided in the stretchable region 80 continuing from the non-stretchable region 70. The indication 71 may correspond to an indication known in a field of the absorbent article, for example, a pattern for decoration (including a tiny picture or a character), a function indicator such as a usage method, usage assistance, a size, etc., or a mark indication such as a manufacturer, a product name, a characteristic function, etc. In an illustrated embodiment, the applied indication 71 is a flower pattern corresponding to a plant pattern. However, it is possible to use various types of patterns such as an abstract pattern, an animal pattern, and a natural phenomenon pattern.

The elastic film 30 may be composed of any resin film having elasticity. For example, it is possible to use a film obtained by processing a blend of one or two or more types of thermoplastic elastomers such as a styrene type elastomer, an olefin type elastomer, a polyester type elastomer, a polyamide type elastomer, a polyurethane type elastomer, etc. in a film shape using extrusion molding such as a T-die method, an inflation method, etc. In addition, it is possible to use a film in which a large number of holes or slits are formed for ventilation in addition to a nonporous film. In particular, it is preferable when the elastic film 30 has a tensile strength in the stretching and contracting direction of 8 to 25 N/35 mm, tensile strength in the direction orthogonal to the stretching and contracting direction of 5 to 20 N/35 mm, tensile elongation in the stretching and contracting direction of 450 to 1,050%, and tensile elongation in the direction orthogonal to the stretching and contracting direction of 450 to 1,400%. The tensile strength and the tensile elongation (elongation at break) refer to values measured at an initial chuck interval to 50 mm and a speed of testing of 300 mm/min with a tensile tester (for example, AUTOGRAPH-G100N available from SHIMADZU) in accordance with JIS K 7127: 1999 "Plastics—Determination of tensile properties—" except that the specimen is formed in a rectangular shape having a width of 35 mm and a length of 80 mm. The thickness of the elastic film 30 is not particularly restricted. However, the thickness is preferably in a range of about 20 to 40 μm. In addition, the basis weight of the elastic film 30 is not particularly restricted. However, the basis weight is preferably in a range of about 30 to 45 $g/m^2$, and particularly preferably in a range of about 30 to 35 $g/m^2$.

Figure 8:
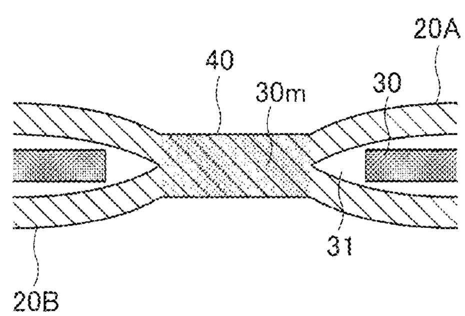
FIG. 8 is a cross-sectional view schematically illustrating a cross section of a main part of the outer body stretched to some extent in a width direction.
Figure 8:
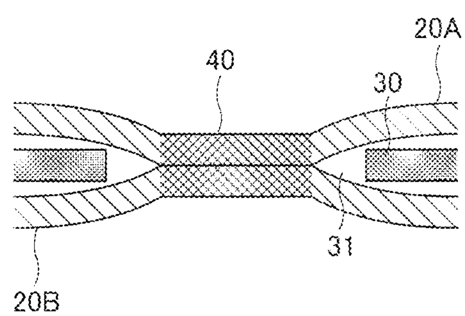
Figure 8:
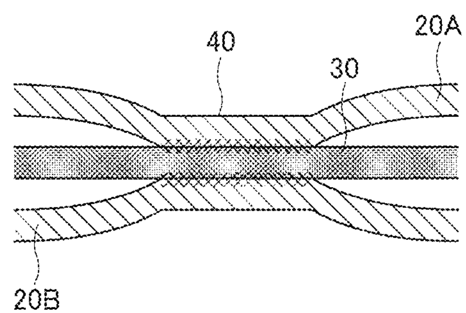

The first sheet layer 20A and the second sheet layer 20B in the bond portions 40 may be joined by a hot-melt adhesive. However, the sheet layers are preferably joined by joining means based on material welding such as heat sealing, ultrasonic sealing, etc. In a case where the joining means based on material welding is used, the through holes of the elastic film may be formed by extrusion, and the first sheet layer 20A and the second sheet layer 20B may be directly joined by welding at positions of the through holes as described in Patent Literature 1. However, there is a concern that since the peeling strength is low, peeling may occur when a strong force is applied. In addition, in Patent Literature 1, since the through holes of the elastic film are formed by extrusion, the elastic film 30 is not left between the first sheet layer 20A and the second sheet layer 20B as illustrated in FIG. 8(*b*), and there is a concern that extrusion debris (not illustrated) may be movably left around the through holes 31. In addition, unlike Patent Literature 1, as illustrated in FIG. 8(*c*), joining the first sheet layer 20A and the second sheet layer 20B through the elastic film 30 without forming the through holes in the elastic film 30 may be taken into consideration. However, in this case, there is a problem that not only peeling strength is low, and but also air permeability is extremely low since the through holes are not included.

Therefore, when the joining means based on material welding is used, as illustrated in FIG. 8(*a*), it is preferable to adopt a mode in which the first sheet layer 20A and the second sheet layer 20B in the bond portions 40 are joined at least by a melted and solidified material 30*m* of the elastic film 30 among the first sheet layer 20A and the second sheet layer 20B. When the first sheet layer 20A and the second sheet layer 20B are joined using the melted and solidified material 30*m* of the elastic film 30 as an adhesive in this way, a peeling strength becomes high, and it is possible to achieve both high air permeability and high peeling strength.

Figure 19:
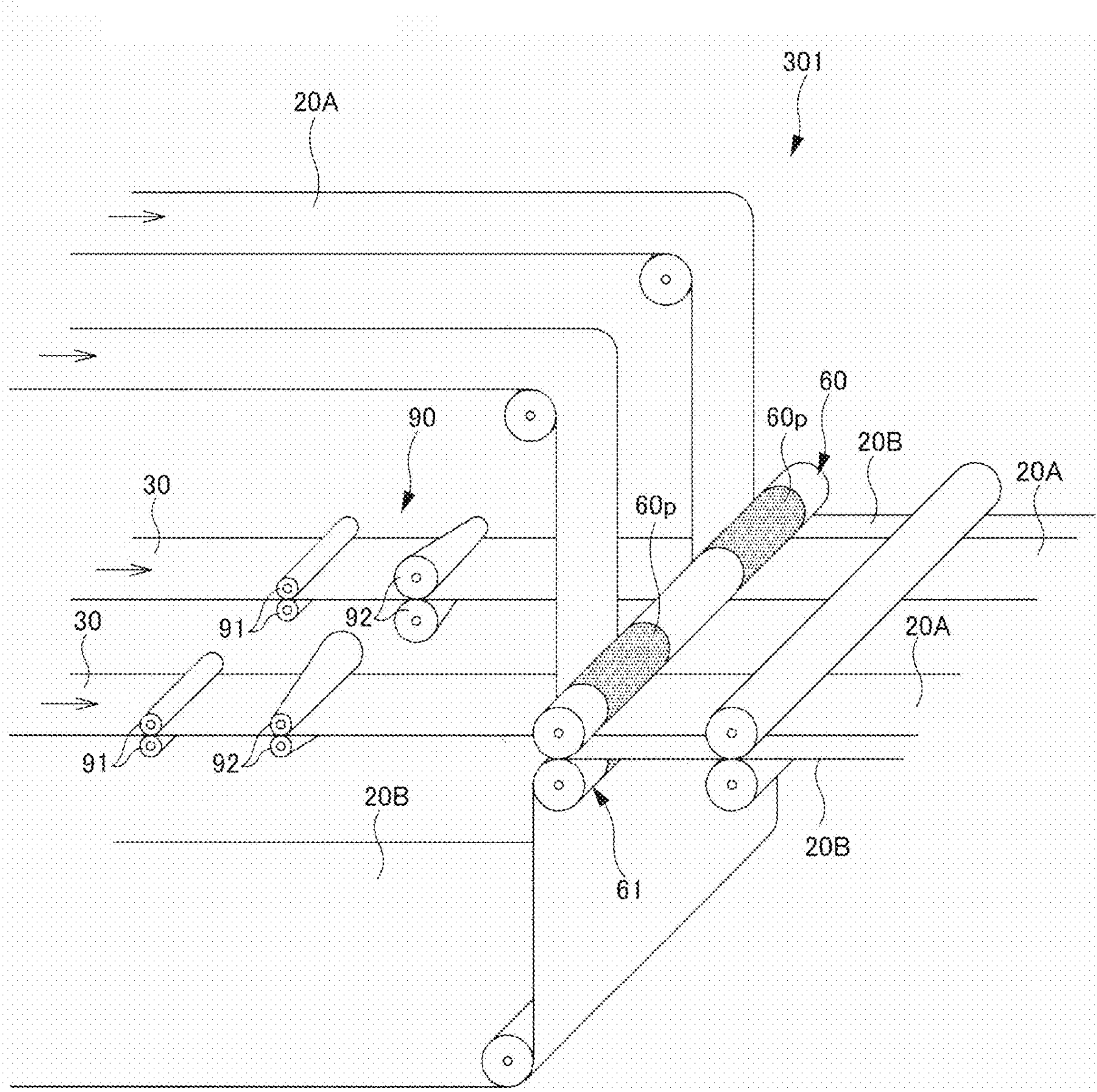
FIG. 19 is a schematic view of an outer body assembly process.

In such a joining structure, for example, as illustrated in FIG. 19, when welding is performed in a predetermined pattern of the bond portions 40 in a state in which the elastic film 30 is interposed between the first sheet layer 20A and the second sheet layer 20B while being stretched in the stretching and contracting direction, the elastic film 30 may be melted at a large number of positions to form the through holes 31, and manufacture may be simply and efficiently performed using a method of joining the first sheet layer 20A and the second sheet layer 20B by at least solidification of the melted material of the elastic film 30 at positions of the through holes 31. In this case, in the natural length state, the shape/area of each of the bond portions 40 are substantially equal to the shape/area of each of the through holes 31. FIG. 19 illustrates an example using a heat sealing device. A material to be processed, while in the material, the elastic film 30 is interposed between the first sheet layer 20A and the second sheet layer 20B, is fed between a seal roll 60 having a large number of pressing protrusions 60*p* arranged in the above pattern of the bond portions 40 on an outer surface thereof and an anvil roll 61 which is disposed to face the seal roll 60 and has a smooth surface, and the pressing protrusions 60*p* are heated. In this way, the elastic film 30 is melted only where pressed in the thickness direction between the pressing protrusions 60*p* and an outer surface of the anvil roll 61 to form the through holes 31, and the first sheet layer 20A and the second sheet layer 20B are joined at least by the solidification of the melted material of the elastic film 30 at the positions of the through holes 31. However, another device such as ultrasonic sealing may be used as long as the elastic film 30 is melted in a desired pattern to form the through holes 31, and the first sheet layer 20A and the second sheet layer 20B are joined at least by solidification of the melted material of the elastic film 30 at the positions of the through holes 31.

Figure 16:
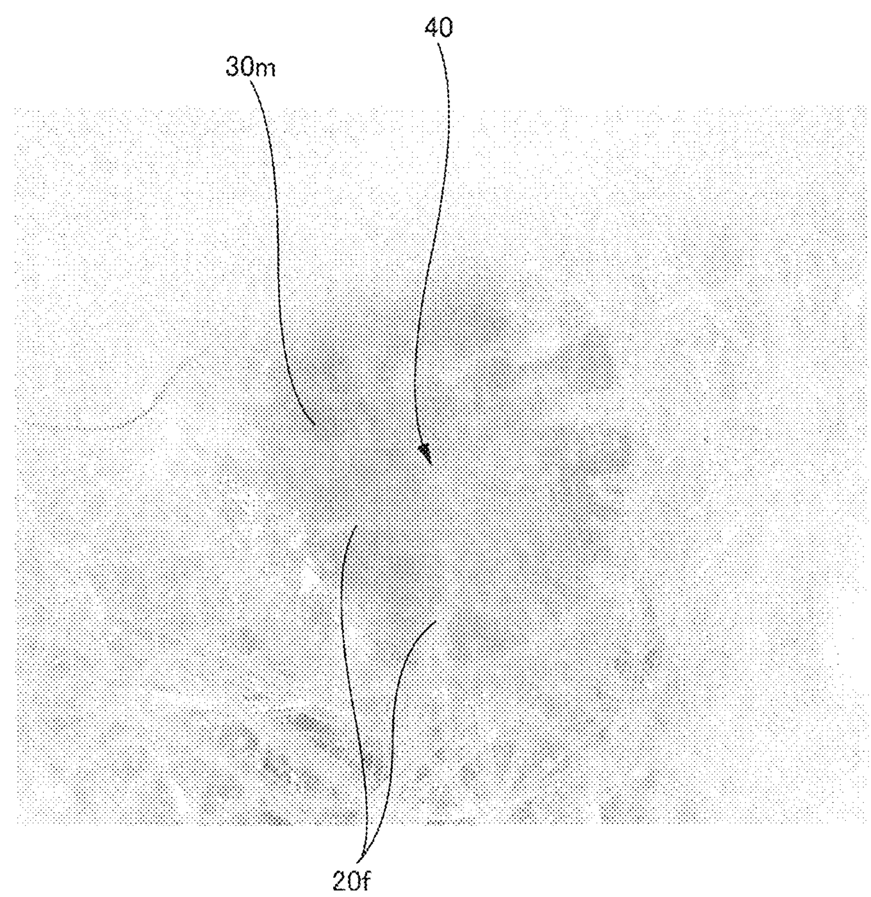
FIG. 16 is an enlarged photograph of a bond portion.
Figure 17:
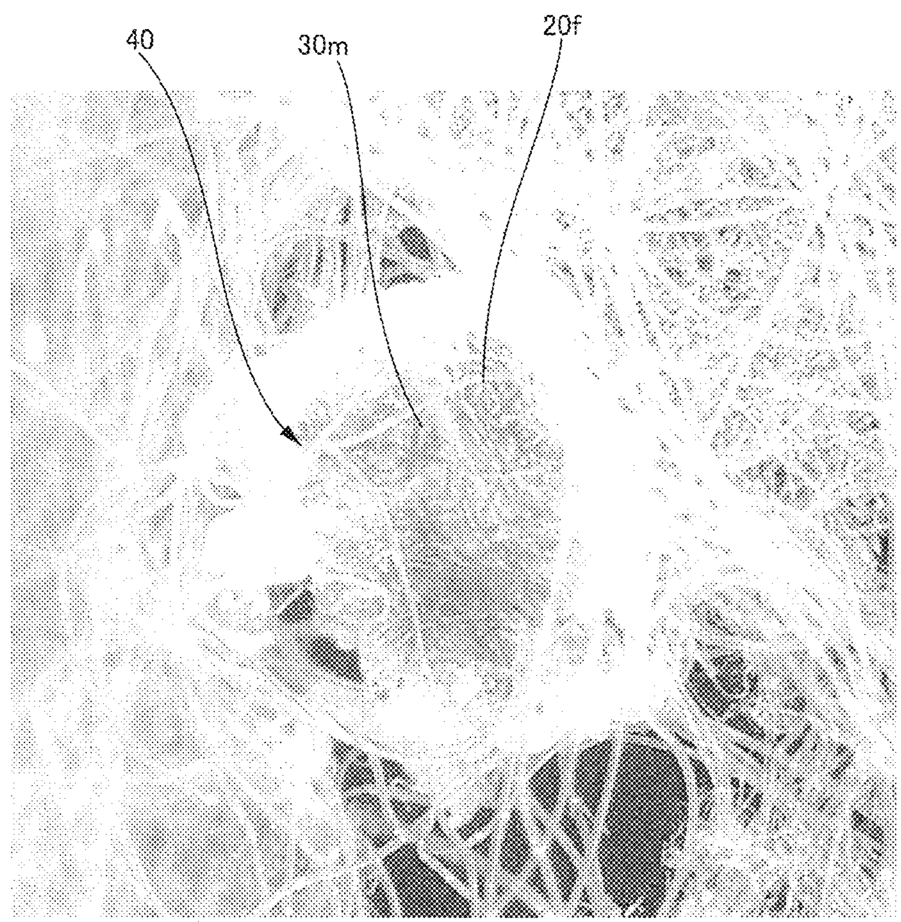
FIG. 17 is an enlarged photograph of a bond portion in a state in which a first sheet layer and a second sheet layer are peeled.

It is possible to appropriately determine a relation of a melting point of the elastic film 30, melting points of the first sheet layer 20A and the second sheet layer 20B, and a processing temperature at a welding position. However, rather than to set the melting points of the first sheet layer 20A and the second sheet layer 20B to be lower than or equal to the melting point of the elastic film 30, melt and combine the whole of the first sheet layer 20A and the second sheet layer 20B and the whole elastic film 30 at the welding positions, and form the bond portions 40, it is preferable to set the melting points of the first sheet layer 20A and the second sheet layer 20B to be higher than the melting point of the elastic film 30, melt the elastic film 30 at the welding position, and not to melt a part of the first sheet layer 20A and the second sheet layer 20B or not to melt a whole of the first sheet layer 20A and the second sheet layer 20B. In other words, as understood from FIG. 16 and FIG. 17, a latter case corresponds to a structure in which fibers 20*f* of the first sheet layer 20A and the second sheet layer 20B continuing from around the bond portions 40 are left, and the first sheet layer 20A and the second sheet layer 20B are joined by the melted and solidified material 30*m* of the elastic film 30, which has infiltrated and solidified among the first sheet layer 20A and the second sheet layer 20B. Further, improved adhering of the melted and solidified material of the elastic film to the first sheet layer and the second sheet layer is obtained, and strength of the first sheet layer 20A and the second sheet layer 20B rarely decreases. Thus, peeling strength is further enhanced. This situation in which "a part of the first sheet layer 20A and the second sheet layer 20B is not melted" includes a mode in which for all fibers of the bond portions, a core (including a central portion of each component fiber of a conjugate fiber in addition to a core of the conjugate fiber) remains while a surrounding portion (including a portion on a surface layer side of each component fiber of a conjugate fiber in addition to a sheath in the conjugate fiber) melts; a mode in which some fibers do not melt at all while all remaining fibers melt; or a mode in which a core remains while a surrounding portion melts.

From this point of view, the melting point of the elastic film 30 is preferably about 80 to 145° C., the melting points of the first sheet layer 20A and the second sheet layer 20B are preferably about 85 to 190° C., particularly, 150 to 190° C., and a difference between the melting points of the first sheet layer 20A and the second sheet layer 20B and the melting point of the elastic film 30 is preferably about 60 to 80° C.

Figure 24:
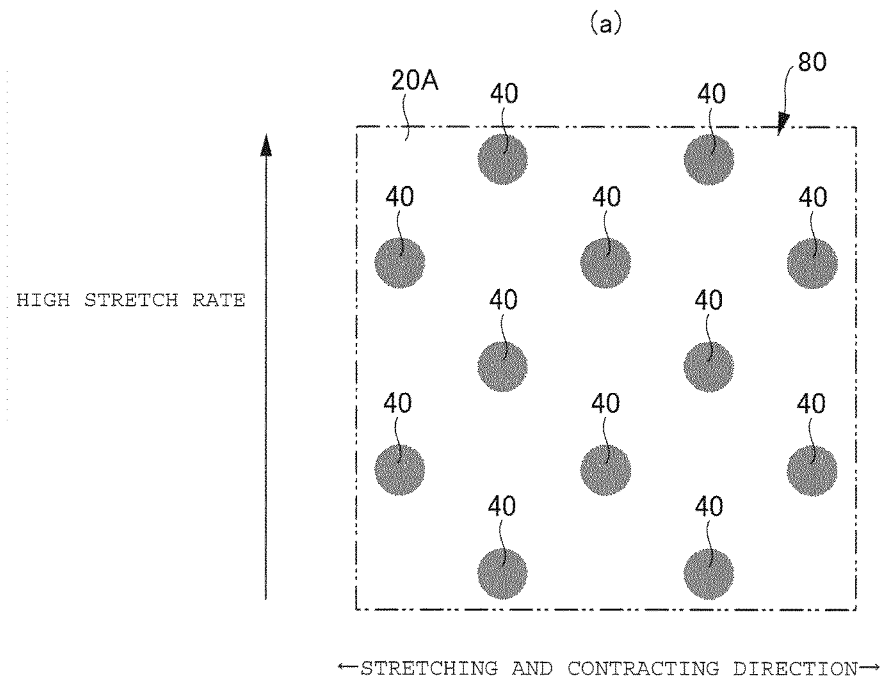
FIG. 24(*a*) is an explanatory diagram illustrating the completely spread state, and FIG. 24(*b*) is an explanatory diagram illustrating a state after contraction.
Figure 24:
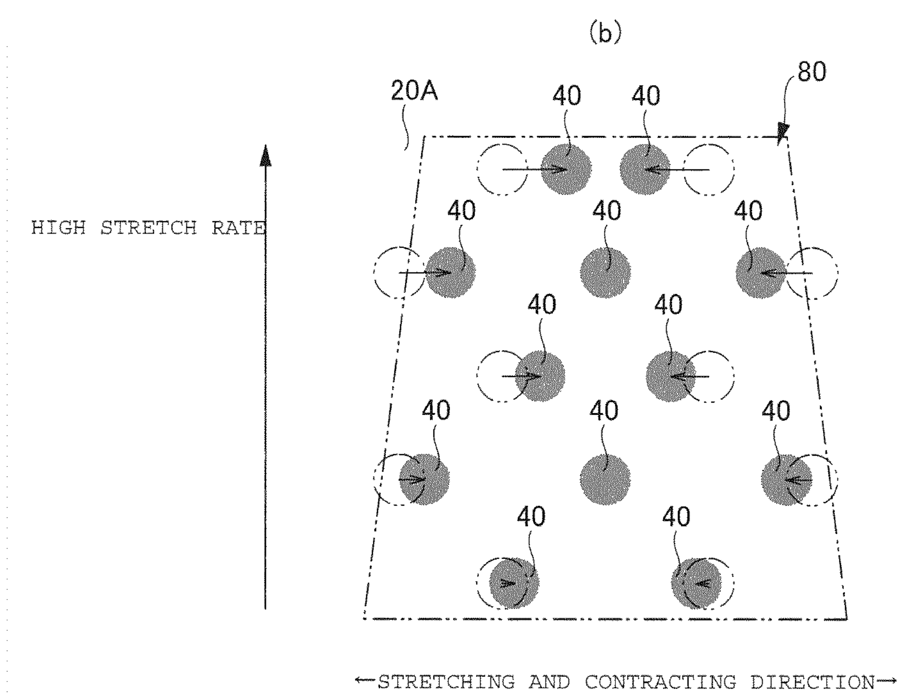

Characteristically, in the stretchable structure 20X of the elastic film 30 described above, the elastic film 30 extends up to the waist portion 23. Further, as a height of a stretch rate is illustrated by a length of a two-dot chain line arrow in FIG. 2, in a state in which the elastic film 30 is stretched in the stretching and contracting direction at a stretch rate continuously increasing from the crotch side toward the waist opening side, the first sheet layer 20A and the second sheet layer 20B are joined. Here, to facilitate understanding, as a state of being extended to an elastic limit in the stretching and contracting direction is illustrated in FIG. 24(*a*), the stretchable region 80 in which the bond portions 40 are arranged in the same pattern is assumed. Then, the first sheet layer 20A and the second sheet layer 20B are joined in a state in which the elastic film 30 is stretched at a stretch rate continuously changing in the direction orthogonal to the stretching and contracting direction of the stretchable region 80. Thus, as illustrated in FIG. 24(*b*), in a contraction state, the contraction increases in a part in which a stretch rate is high in fixing the elastic film 30, that is, at an upper side of the figure, and a distance between the adjacent two bond portions 40 becomes narrow. For this reason, in a stretched state, a contraction force increases toward the upper side of the figure. Therefore, as is understood from a state after manufacture illustrated in FIG. 18, in a natural length state, an external shape in which a width becomes narrow toward the waist opening side is obtained. Further, even when a separate rubber thread is not provided in the waist portion 23, a contraction force of the waist portion 23 increases in a worn state. In other words, it is possible to change elasticity depending on the part in the direction orthogonal to the stretching and contracting direction, and to obtain more preferable fitness.

Even when the elastic film 30 is provided up to the waist portion 23 as in the illustrated embodiment, a separate elongated elastically stretchable member may be provided in the waist portion 23. In addition, even when the elastic film 30 is not provided up to the waist portion, the separate elongated elastically stretchable member may be provided in the waist portion 23. In this case, the elastic film 30 may be allowed to extend up to the waist portion 23. Conventionally, in an underpants-type disposable diaper in which the elongated elastically stretchable member is provided in the waist portion 23, the waist portion 23 remarkably contracts when compared to a part on the crotch side thereof, and thus appearance deteriorates. However, when the elastic film is fixed at the stretch rate continuously changing and the elongated elastically stretchable member of the waist portion is combined with the elastic film fixed in this way, appearance is excellent due to continuous change in the contraction amount. When the elongated elastically stretchable member is provided in the waist portion 23, three or more, preferably five or more elongated elastically stretchable members are disposed at intervals of about 3 to 8 mm to form a predetermined stretchable zone. A stretch rate of the elastic member provided in the waist portion 23 in fixing may be appropriately determined. However, the stretch rate may be set to about 230 to 320% in the case of normal adult use. One or a plurality of belt shaped elastic members may be used as the elastic member provided in the waist portion 23.

The extent of change in the stretch rate of the elastic film 30, in fixing the same in the stretchable structure 20X, may be appropriately determined. However, it is preferable that in a product, an elongation at an elastic limit of a portion having the highest elongation (approximately equal to a stretch rate in fixing the same in the stretchable structure) is set to 1.1 to 1.5 times an elongation at an elastic limit of a portion having the lowest elongation. More specifically, for example, in the case of the illustrated embodiment, an elongation at an elastic limit of the waist portion may be set to about 250 to 295%, and an elongation at an elastic limit of the part on the crotch side thereof may be set to about 200 to 250%.

Figure 18:
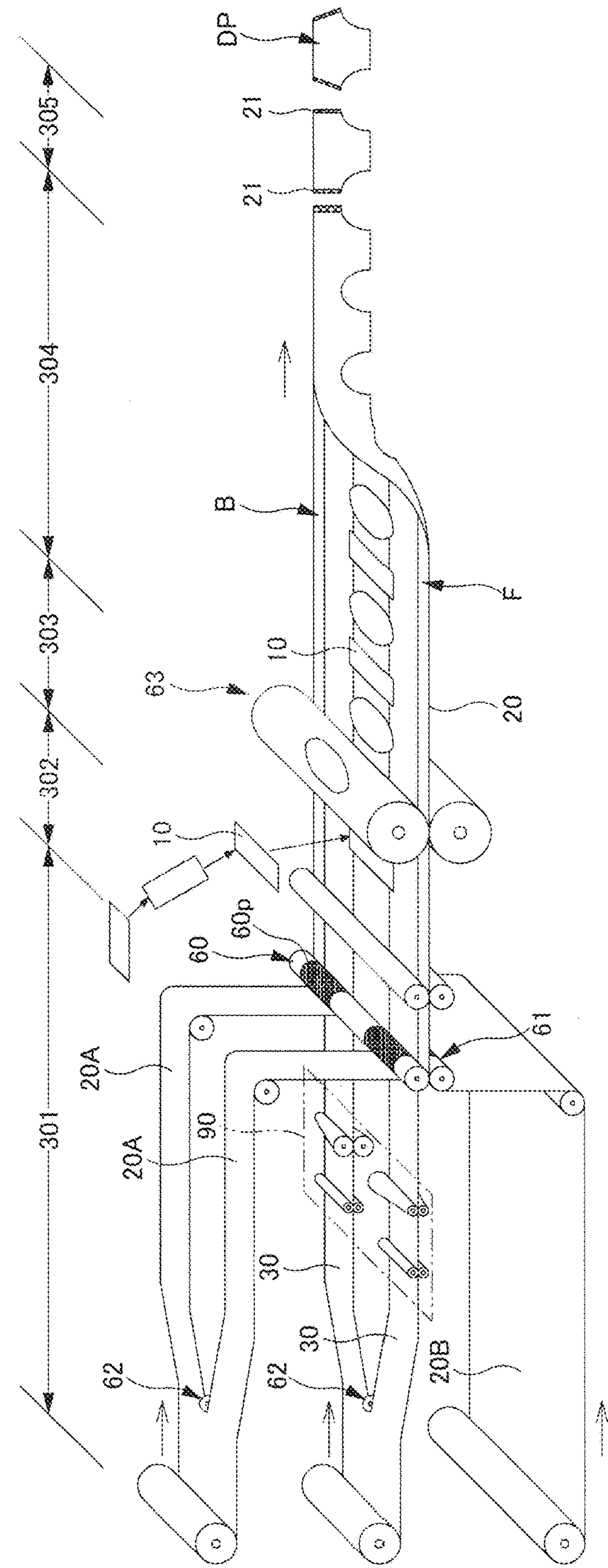
FIG. 18 is a schematic view illustrating a manufacturing flow of the underpants-type disposable diaper.

FIG. 18 illustrates an example of a method of manufacturing an underpants-type disposable diaper having substantially the same structure as that of the above description. This production line corresponds to a horizontal flow mode in which the width direction of the diaper is MD (line flow direction), and the outer body 20 is formed thereon. After the inner body 10 manufactured on another line is attached to the outer body 20, both side portions of front and back outer bodies 20 are joined by folding at a center in the front-back direction, and division into individual diapers DP is performed. For the sake of easy understanding, the same name and reference symbol as those of a member after manufacture are used for members that are continuous in a manufacturing process.

More specifically, this production line includes an outer body assembly process 301, an inner body attachment process 302, a leg opening punching process 303, a folding process 304, and a side portion joining/separation process 305. Among these processes, the outer body assembly process 301 is a characteristic process. Specifically, in the outer body assembly process 301, as enlarged and illustrated in FIG. 19, the first sheet layer 20A and the second sheet layer 20B that are continuous in belt-shaped manner with predetermined widths are fed to sealing devices 60 and 61 and such that the first sheet layer 20A and the second sheet layer 20B are bonded along a continuing direction thereof, and the elastic film 30 that is continuous in belt-shaped manner with predetermined width passes through a stretch roll group 90 and is fed to the sealing devices by being interposed between the first sheet layer 20A and the second sheet layer 20B in a state of being stretched in the MD. In the illustrated embodiment, one sheet material is segmented into two parts by a slitter 62 to feed the first sheet layer 20A as separate front and back parts. However, the sheet material may be fed as separate front and back parts, or a unified front and back sheet material may be fed similarly to the second sheet layer 20B without separating the first sheet layer 20A into front and back parts. Similarly, in the illustrated embodiment, one elastic film 30 is segmented into two parts by the slitter 62 to feed the elastic film 30 as separate front and back parts. However, the elastic film 30 may be fed as separate front and back parts, or a unified front and back elastic film 30 may be fed, without separating the elastic film 30 into front and back parts.

Figure 20:
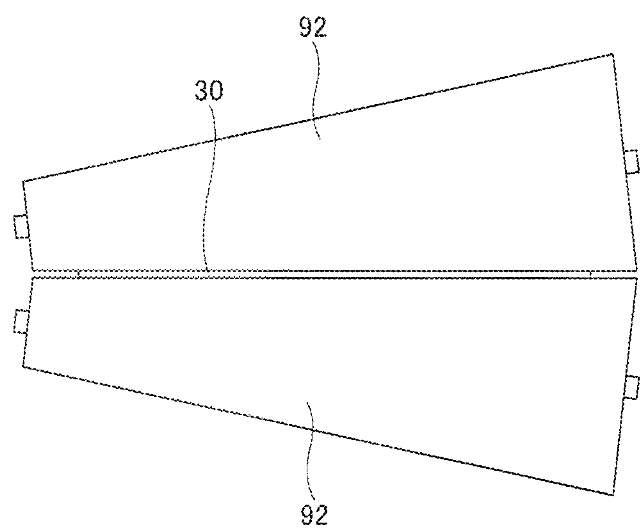
FIG. 20 is a side view of a second nip roll viewed from an MD (Machine Direction) side.

Characteristically, in stretching the elastic film 30 in the MD by the stretch roll group 90, the elastic film 30 is stretched at a stretch rate that continuously changing in CD (Cross Direction) (a direction orthogonal to the MD). The stretch roll group 90 includes first nip rolls 91 and second nip rolls 92 disposed at intervals in the MD. The first nip roll 91 is a cylindrical roll and the second nip roll 92 is a truncated cone roll. The first nip rolls 91 and the second nip rolls 92 are driven at the same revolutions per minutes (RPM), and both the first nip rolls 91 and the second nip rolls 92 feed the elastic film 30 by interposing the elastic film 30 between the rolls, respectively. However, each of the second nip rolls 92 is disposed such that the crotch side has a larger diameter as illustrated in FIG. 20, and thus a feeding speed of the elastic film 30 increases from the waist side toward the crotch side. However, this feeding speed is slower than a feed speed in the sealing devices 60 and 61 at a subsequent stage. As a result, the elastic film 30 is stretched in the MD at a stretch rate increasing from the crotch side toward the waist side between the sealing devices 60 and 61 and the second nip roll 92. In this state, the elastic film 30 is sealed by the sealing devices 60 and 61, and the outer body 20 in which the leg opening is to be formed is formed.

As described above, the sealing devices 60 and 61 of the illustrated embodiment correspond to an example using a heat sealing device. The first sheet layer 20A, the elastic film 30 stretched in the MD at the stretch rate increasing from the crotch side toward the waist side, and the second sheet layer 20B are interposed by a seal roll 60 having a plurality of pressing protrusions 60*p* arranged in the pattern of the bond portions 40 described above on an outer circumference surface, and an anvil roll 61 which is disposed to face the seal roll 60 and has a smooth surface. Further, the elastic film 30 is melted only in a part pressed in the thickness direction between the pressing protrusions 60*p* and an outer circumference surface of the anvil roll 61 by heating the pressing protrusions 60*p*, thereby forming the through holes 31, and the first sheet layer 20A and the second sheet layer 20B are bonded by welding at positions of the through holes 31. Another device such as an ultrasonic sealing device may be used as the sealing device.

Thereafter, the underpants-type disposable diaper may be formed by adopting a known manufacturing process. In the illustrated embodiment, the inner body 10 manufactured on another line is fed at a predetermined interval in the MD to the outer body 20 formed by the sealing devices 60 and 61 in the inner body attachment process 302, and is joined to the outer body 20 using appropriate means such as a hot-melt adhesive, heat sealing, etc. In this way, inner assembly bodies 10 and 20 are formed. After (or before) the inner body attachment process 302, in the leg opening punching process 303, leg openings are formed in order by a cutter device 63. Thereafter, in the folding process 304, the inner assembly bodies 10 and 20 are folded at a center in the CD. Then, in the side portion joining/separation process 305, the outer body 20 of the front body F and the outer body 20 of the back body B are joined at portions corresponding to both side portions of the individual diapers DP to form the side seal portion 21, and the outer body 20 is cut at a boundary of the individual diapers to obtain the individual diapers DP. As described above, each of the manufactured individual diapers DP has an external shape in which the width becomes narrow toward the waist side in the natural length state.

The illustrated example corresponds to an example in which the elastic film stretchable structure 20X is applied to the stretchable structure of the lower-torso region T and the intermediate region L of the outer body 20. However, it is possible to make appropriate changes by adopting a mode in which the elastic film stretchable structure is applied except for the waist portion 23, another mode in which the elastic film stretchable structure 20X is not provided in the intermediate region L between the lower-torso region T of the front body F and the lower-torso region T of the back body B and the like. In addition, the above-described stretchable structure 20X may be applied to another elastic portion such as a three-dimensional gather, a plane gather, etc. generally used for a waist, a fastening tape, and an absorbent article of a tape-type disposable diaper in addition to the underpants-type disposable diaper. In addition, even though the non-stretchable region 70 is included in the present embodiment, it is possible to adopt a mode in which the whole elastic film 30 stretchable structure 20X is used as the stretchable region 80 and the non-stretchable region is not included. Furthermore, even though the stretching and contracting direction is regarded as the width direction in the illustrated embodiment, the stretching and contracting direction may be set to both the width direction and the front-back direction.

(Front and Back Cover Sheets)

As illustrated in FIG. 1 and FIG. 4, front and back cover sheets 50 and 60 may be provided to cover front and back end portions of the inner body 10 attached on the internal surface of the outer body 20 to prevent leakage from the front and back edges of the inner body 10. An illustrated embodiment will be further described in detail. The front cover sheet 50 extends over the whole width of the front body F on the internal surface of the front body F from the internal surface of the folded part 20C at a waist side end of the front body F to a position overlapping with the front end portion of the inner body 10. The back cover sheet 50 extends over the whole width of the back body B on the internal surface of the back body B from the internal surface of the folded part 20C at a waist side end of the back body B to a position overlapping with the back end portion of the inner body 10. When slight non-adhesive portions are provided over the whole width (or only at a central part) at side edge portions of the front and back cover sheets 50 and 60 at the crotch side, leakage of the adhesive can be prevented and these non-adhesive portions may function as barriers against leakage when slightly raised from the surface sheet.

When the front and back cover sheets 50 and 60 are provided as separate components as illustrated in FIG. 1 and FIG. 4, although high degree of freedom for choosing material is advantageously obtained, additional materials and manufacturing processes are disadvantageously needed. For this reason, in another embodiment, the folded parts 20C formed by folding back the outer body 20 toward the internal surface side of the diaper may be respectively extended to portions overlapping the inner body 10, to form portions equivalent to the front and back cover sheets 50 and 60.

<Others>

Figure 21:
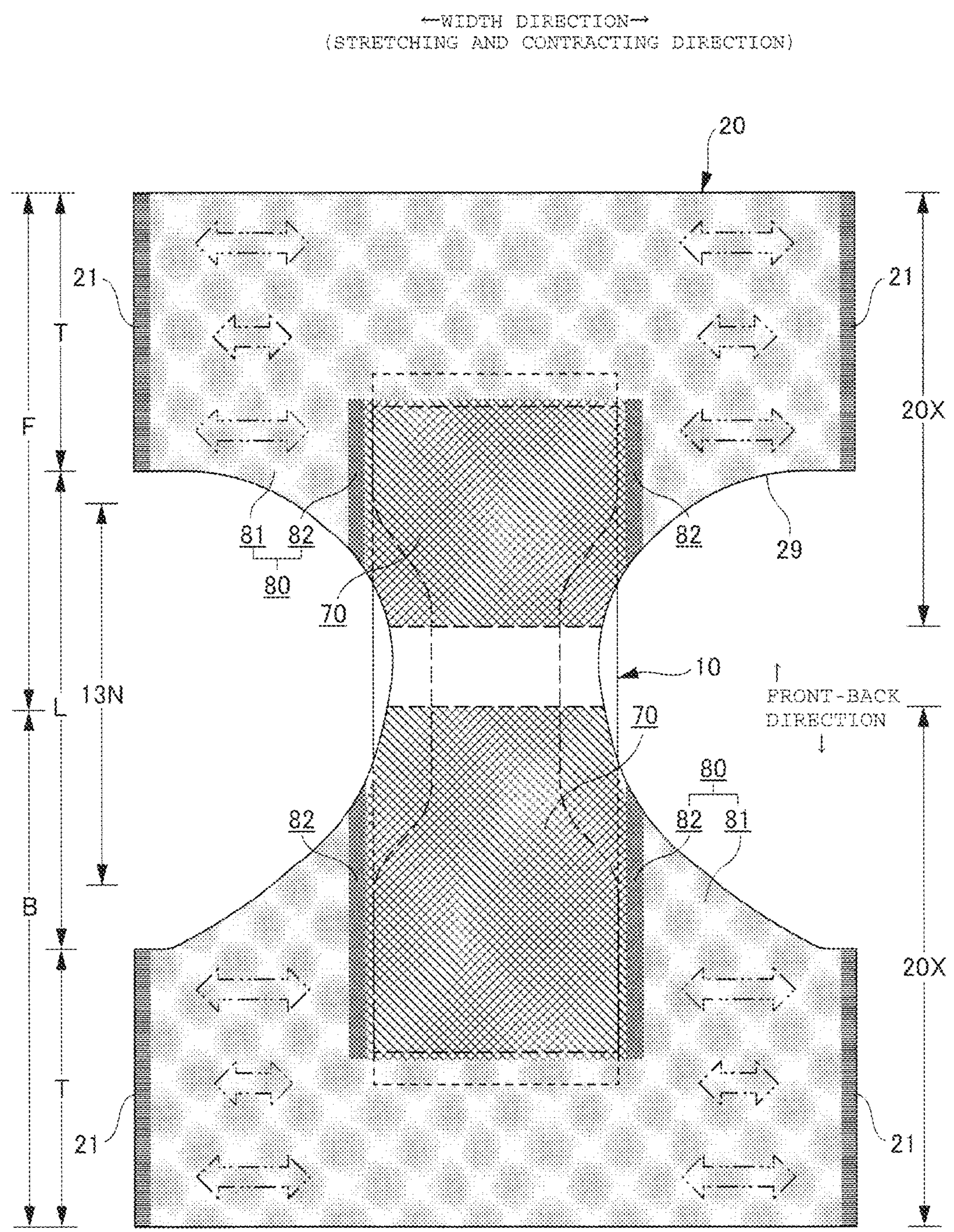
FIG. 21 is a plan view (external surface side) of the underpants-type disposable diaper in the completely spread state.
Figure 22:
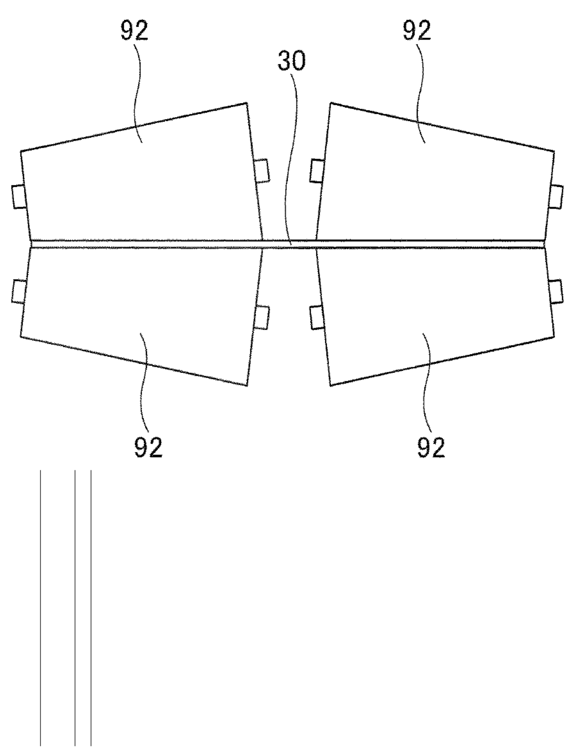
FIG. 22 is a side view of the second nip roll viewed from the MD side.
Figure 23:
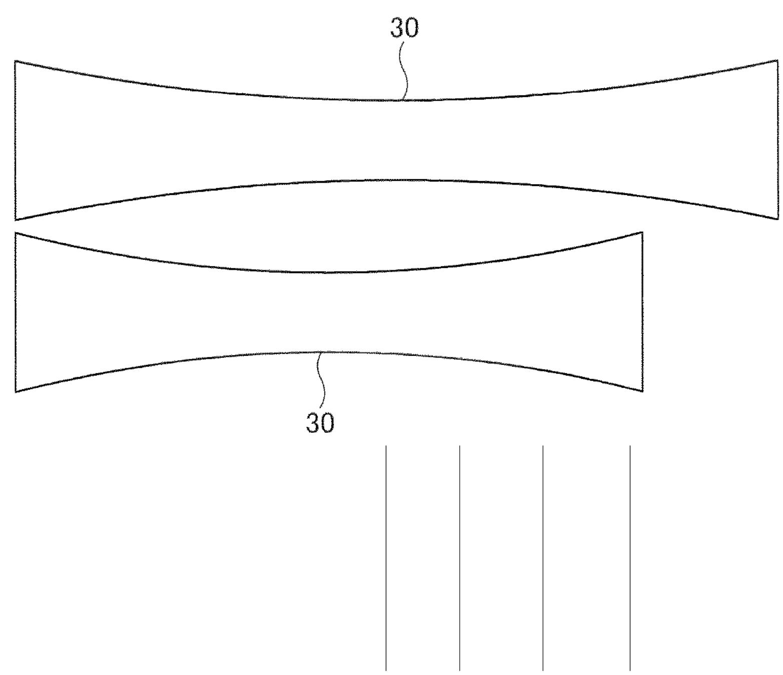
FIG. 23 is an explanatory diagram illustrating WIDTH-DECREASING of the elastic films.

The above example adopts a mode in which the stretch rate of the elastic film 30 increases from the crotch side toward the waist side. However, conversely, it is possible to adopt a mode in which the stretch rate increases from the waist side toward the crotch side. Further, as a level of a stretch rate is illustrated by a length of a two-dot chain line arrow in FIG. 21, it is possible to adopt a mode in which the stretch rate increases from the middle in the vertical direction toward the crotch side and the waist side. For example, the latter mode may be formed by disposing a truncated cone roll 92 whose diameter decreases from the middle in the CD toward one side in the CD and a truncated cone roll 92 whose diameter decreases from the middle in the CD toward another side in the CD illustrated in FIG. 22 as the second nip roll 92 in a manufacturing flow illustrated in FIG. 18. As understood from these examples, the present invention is not limited to the above examples as long as the first sheet layer 20A and the second sheet layer 20B are joined together in a state in which the elastic film 30 is stretched in the stretching and contracting direction at a stretch rate continuously changing in the direction orthogonal to the stretching and contracting direction of the stretchable region 80.

Description of Terms in Specification

The terms used in the specification have the following meanings unless otherwise stated.

The "stretch rate" represents a value relative to the natural-length set to be 100%.

The "Basis weight" is determined as follows: After the sample or test piece is preliminarily dried, it is allowed to stand in a testing chamber or machine under the standard condition (temperature: 20±5° C., relative humidity: 65% or less) until the constant mass. The preliminary drying represents that the sample or test piece reaches constant mass in an environment within a relative humidity of 10 to 25% and at a temperature not exceeding 50° C. The fiber of an official regain of 0.0% does not need preliminary drying. A cut sample with a size of 200 mm by 250 mm (±2 mm) is prepared from the test piece after the constant mass with a cutting template (200 mm by 250 mm, ±2 mm). The sample is weighed and the weight is multiplied by 20 into the weight per square meter. The resulting value is defined as basis weight.

A "thickness" is automatically determined with an automatic thickness gauge (KES-G5 handy compression measurement program) under the conditions of a load of 10 gf/cm$^2$ and a pressurization area of 2 cm$^2$.

In the absence of description about an environmental condition in a test or measurement, the test or measurement is performed in a test room or a device in a standard state (temperature 20±5° C., relative humidity 65% or less in a test location).

INDUSTRIAL APPLICABILITY

The invention may be generally used for an absorbent article having a stretchable region such as a sanitary napkin, various disposable diapers such as a tape-type disposable diaper, an underpants-type disposable diaper, etc. in addition to the underpants-type disposable diaper in the above example, etc.

B . . . back body, F . . . front body, T . . . lower-torso region, L . . . intermediate region, 10 . . . inner body, 11 . . . liquid-pervious front surface sheet, 12 . . . liquid impervious back surface side sheet, 13 . . . absorber, 13N . . . narrower portion, 14 . . . package sheet, 15 . . . gather nonwoven fabric, 16 . . . gather elastic member, 20 . . . outer body, 20A . . . first sheet layer, 20B . . . second sheet layer, 20C . . . folded part, 20X . . . stretchable structure, 21 . . . side seal portion, 23 . . . waist portion, 25 . . . contraction wrinkle, 29 . . . leg line, 30 . . . elastic film, 31 . . . through hole, 40 . . . bond portion, 70 . . . non-stretchable region, 71 . . . indication, 80 . . . stretchable region, 81 . . . main stretchable section, 82 . . . buffer stretchable section.

The invention claimed is:

1. An absorbent article comprising a stretchable region having an elastic film between a first sheet layer made of a nonwoven fabric and a second sheet layer made of a nonwoven fabric, wherein in the stretchable region, the first sheet layer and the second sheet layer are joined via through holes formed in the elastic film at bond portions arranged at intervals in a first direction and a second direction orthogonal thereto, the stretchable region is stretchable in the second direction from one end to another end in the first direction, in a stretched state of the stretchable region, as the elastic film is stretched between the bond portions, a distance between the bond portions is widened, and the elastic film is configured to stretch up to a completely spread state, such that any wrinkles forming between the first sheet layer and the second sheet layer are removed as the stretchable region is stretched, and in the stretchable region, an elongation at an elastic limit in the second direction at each position in the first direction continuously changes as the position in the first direction continuously changes.

2. The absorbent article according to claim 1, wherein the absorbent article is an underpants-type disposable diaper comprising an outer body included in a front body and a back body, and an inner body that includes an absorber and is fixed to an internal surface of the outer body, wherein both side portions of the outer body in the front body are respectively joined to both side portions of the outer body in the back body to define side seal portions, and a lower-torso region in an annular shape, a waist opening and a pair of right and left leg openings are thereby formed, at least one of the outer body of the front body and the outer body of the back body has the stretchable region being stretchable in a width direction in a portion of the lower-torso region including at least a waist portion, and in the stretchable region, an elongation at an elastic limit in the width direction at each position in a front-back direction is continuously increasing as the position of the front-back direction continuously changes from a crotch side toward a waist opening side.

3. The absorbent article according to claim 1, wherein an area of each of the bond portions in the stretchable region is in a range of 0.14 to 3.5 mm2, an area of an opening of each of the through holes in a natural length state is 1 to 1.5 times the area of each of the bond portions, an area rate of the bond portions in the stretchable region is in a range of 1.8 to 22.5%, the stretchable region corresponds to a region in which the bond portions are arranged in the same pattern, and a portion having a highest elongation at an elastic limit in the stretchable region has a stretch rate set to 1.1 to 1.5 times the stretch rate of a portion having a lowest elongation at the elastic limit in the stretchable region.

4. A method of manufacturing an absorbent article including a stretchable region having an elastic film between a first sheet layer made of a nonwoven fabric and a second sheet layer made of a nonwoven fabric, wherein in the stretchable region, the first sheet layer and the second sheet layer are joined via through holes formed in the elastic film at bond portions arranged at intervals in a first direction and a second direction orthogonal thereto, the stretchable region is stretchable in the second direction from one end to another end in the first direction, in the stretched state of the stretchable region, as the elastic film is stretched between the bond portions, a distance between the bond portions is widened, and the elastic film is configured to stretch up to a completely spread state, such that any wrinkles forming between the first sheet layer and the second sheet layer are removed as the stretchable region is stretched, in forming the stretchable region, in a state in which the elastic film is interposed between the first sheet layer and the second sheet layer while being stretched in a machine direction, the elastic film is melted to form the through holes at a plurality of positions arranged at intervals in the machine direction and a cross direction orthogonal thereto, and the first sheet layer and the second sheet layer are joined via the through holes, and in stretching the elastic film in the machine direction, a stretch rate of the elastic film in the machine direction at each position in the cross direction continuously changes as the position in the cross direction continuously changes.

5. An underpants-type disposable diaper comprising:

a first outer body included in a front body having front side portions and a second outer body included in a back body having back side portions;

wherein each of the front side portions is joined to one of the back side portions to thereby define side seal portions, a waist opening side, a crotch side, and an internal surface of the underpants-type disposable diaper;

an inner body includes an absorber and is fixed to the internal surface;

at least one of the first outer body and the second outer body has a stretchable region comprising an elastic film between a first sheet layer made of a nonwoven fabric and a second sheet layer made of a nonwoven fabric;

the first sheet layer and the second sheet layer are joined via through holes formed in the elastic film at bond portions arranged at intervals in a width direction and a front-back direction orthogonal thereto;

in stretching the elastic film in the width direction while being stretched, elasticity of the stretchable region continuously changes in the front-back direction from the crotch side to the waist opening side so that the elastic film is extended in the width direction from the crotch side to the waist opening side; and in the stretched state, as the elastic film is stretched between the bond portions, a distance between the bond portions is widened, and the elastic film is configured to stretch up to a completely spread state, such that any wrinkles forming between the first sheet layer and the second sheet layer are removed as the stretchable region is stretched.

6. The underpants-type disposable diaper according to claim 5, wherein at least one of the first outer body and the second outer body has the stretchable region in a portion of the lower-torso region including at least a waist portion.

7. The underpants-type disposable diaper according to claim 5, wherein:

an area of each of the bond portions in the stretchable region is in a range of 0.14 to 3.5 mm2;

an area of an opening of each of the through holes in a natural length state is 1 to 1.5 times the area of each of the bond portions;

an area rate of the bond portions in the stretchable region is in a range of 1.8 to 22.5%;

the stretchable region corresponds to a region in which the bond portions are arranged in the same pattern; and a portion having a highest elongation at an elastic limit in the stretchable region has a stretch rate set to 1.1 to 1.5 times the stretch rate of a portion having a lowest elongation at the elastic limit in the stretchable region.

8. The underpants-type disposable diaper according to claim 5, further comprising:

a non-stretchable region; and wherein the first sheet layer and the second sheet layer are joined together via through holes formed in the elastic film at a plurality of bond portions arranged at intervals in the width direction and the front-back direction; and wherein area rate of the plurality of bond portions in the non-stretchable region is larger than the area rate of the plurality of bond portions in the stretchable region.

9. The underpants-type disposable diaper according to claim 8, wherein elongation at an elastic limit in the stretchable region is greater than elongation at the elastic limit in the non-stretchable region.

10. The underpants-type disposable diaper according to claim 5, wherein elasticity of the elastic film continuously increases in the front-back direction orthogonal to the width direction.

11. The underpants-type disposable diaper according to claim 10, wherein the elasticity of the elastic film continuously increases from a first end of the elastic film to a second end of the elastic film.

12. The underpants-type disposable diaper according to claim 11, wherein the first end of the elastic film is along the crotch side and the second end of the elastic film is along the waist opening side.

13. The underpants-type disposable diaper according to claim 5, wherein in a stretched state, contraction forces in the elastic film continuously increase in the front-back direction.

14. The underpants-type disposable diaper according to claim 13, wherein in the stretched state, the contraction forces in the elastic film continuously increase from a first end of the elastic film to a second end of the elastic film.

15. The underpants-type disposable diaper according to claim 14, wherein the first end of the elastic film is along the crotch side and the second end of the elastic film is along the waist opening side.

* * * * *